United States Patent
Gollan et al.

(10) Patent No.: US 12,296,165 B2
(45) Date of Patent: May 13, 2025

(54) EJACULATION CONTROL

(71) Applicant: Virility Medical Ltd., Hod-HaSharon (IL)

(72) Inventors: Tal Gollan, Ramat-Gan (IL); Gideon Meiri, Kibbutz Shomrat (IL); Oded Shlomo Kraft-Oz, Haifa (IL)

(73) Assignee: Virility Medical Ltd., Hod-HaSharon (IL)

( * ) Notice: Subject to any disclaimer, the term of this patent is extended or adjusted under 35 U.S.C. 154(b) by 0 days.

(21) Appl. No.: 18/542,883

(22) Filed: Dec. 18, 2023

(65) Prior Publication Data

US 2024/0115858 A1    Apr. 11, 2024

Related U.S. Application Data

(63) Continuation of application No. 16/957,752, filed as application No. PCT/IL2018/051402 on Dec. 27, 2018, now Pat. No. 12,017,067.
(Continued)

(51) Int. Cl.
*A61N 1/36* (2006.01)
*A61F 5/41* (2006.01)
*A61N 1/04* (2006.01)

(52) U.S. Cl.
CPC ............ *A61N 1/36007* (2013.01); *A61F 5/41* (2013.01); *A61N 1/0452* (2013.01);
(Continued)

(58) Field of Classification Search
CPC .............. A61N 1/36007; A61N 1/0452; A61N 1/0456; A61N 1/0476; A61N 1/36031; A61N 1/0492; A61F 5/41; A61F 2005/418
See application file for complete search history.

(56) References Cited

U.S. PATENT DOCUMENTS 5,562,717 A    10/1996  Tippey et al.
7,894,913 B2    2/2011  Boggs et al.
(Continued)

FOREIGN PATENT DOCUMENTS

CA    2913074    12/2014
CN    103550860    2/2014
(Continued)

OTHER PUBLICATIONS

English Summary Dated Sep. 28, 2023 of Notification of Office Action Dated Sep. 13, 2023 From the State Intellectual Property Office of the People's Republic of China Re. Application No. 201880090395.5. (5 pages).
(Continued)

*Primary Examiner* — Rex R Holmes
(74) *Attorney, Agent, or Firm* — The Roy Gross Law Firm, LLC; Roy D. Gross

(57) ABSTRACT

A device for electrifying perineal tissue, including:
a housing shaped and sized to be attached to a perineum surface of a subject between a posterior aspect of the scrotum and the anus of the subject;
at least two electrodes in the housing configured to deliver an electric field to a perineal tissue, wherein the electrodes are positioned entirely between the scrotum and the anus;
a pulse generator in the housing electrically connected to the at least two electrodes, wherein the pulse generator generates an electric field with parameter values selected to affect at least one selected target within the perineal tissue;
a control circuitry in the housing electrically connected to the pulse generator;
a readable and writable memory circuit in the housing electrically connected to the control circuitry, wherein
(Continued)

the readable and writable memory stores indications of at least one electric field parameter and/or at least one treatment program.

20 Claims, 19 Drawing Sheets

Related U.S. Application Data

(60) Provisional application No. 62/610,535, filed on Dec. 27, 2017.

(52) U.S. Cl.
CPC ......... *A61N 1/0456* (2013.01); *A61N 1/0476* (2013.01); *A61N 1/36031* (2017.08); *A61F 2005/418* (2013.01)

(56) References Cited

U.S. PATENT DOCUMENTS

| | | | |
|---|---|---|---|
| 8,876,696 | B2 | 11/2014 | Mikhailenok et al. |
| 9,149,634 | B2* | 10/2015 | Lee ..................... A47K 13/24 |
| 9,370,652 | B2 | 6/2016 | Lin et al. |
| 9,764,010 | B2 | 9/2017 | Nilsson Neijber |
| 10,773,072 | B2 | 9/2020 | Gollan |
| 12,069,658 | B2 | 8/2024 | Takano |
| 2006/0020297 | A1 | 1/2006 | Gerber et al. |
| 2007/0055337 | A1 | 3/2007 | Tanrisever |
| 2008/0161874 | A1 | 7/2008 | Bennett et al. |
| 2009/0182393 | A1 | 7/2009 | Bachinski |
| 2010/0016759 | A1 | 1/2010 | Lavoisier |
| 2013/0006322 | A1 | 1/2013 | Tai |
| 2013/0116742 | A1 | 5/2013 | Lavoisier |
| 2014/0074179 | A1 | 3/2014 | Heldman et al. |
| 2014/0155954 | A1 | 6/2014 | Lee |
| 2014/0324120 | A1 | 10/2014 | Bogie et al. |
| 2015/0290450 | A1 | 10/2015 | Kolb et al. |
| 2015/0335288 | A1* | 11/2015 | Toth ..................... A61B 5/6833 600/391 |
| 2016/0015553 | A1 | 1/2016 | Caldarone |
| 2016/0015962 | A1 | 1/2016 | Shokoueinejad Maragheh et al. |
| 2016/0263376 | A1 | 9/2016 | Yoo et al. |
| 2016/0303370 | A1 | 10/2016 | Sharma |
| 2017/0014632 | A1 | 1/2017 | Kimura |
| 2018/0043157 | A1 | 2/2018 | Sharma |
| 2018/0168919 | A1 | 6/2018 | Fung ..................... A61H 23/02 |
| 2018/0345003 | A1 | 12/2018 | Gollan |
| 2021/0016078 | A1 | 1/2021 | Gollan |
| 2021/0236805 | A1 | 8/2021 | Gollan |

FOREIGN PATENT DOCUMENTS

| | | |
|---|---|---|
| EP | 2237831 | 10/2010 |
| EP | 3131622 | 2/2017 |
| JP | 08-501946 | 3/1996 |
| JP | 2000-167067 | 6/2000 |
| JP | 2011-519646 | 7/2011 |
| JP | 2011-213617 | 10/2011 |
| JP | 2016-523125 | 8/2016 |
| KR | 10-2011-030443 | 3/2011 |
| KR | 10-1416612 | 7/2014 |
| RU | 2207162 | 6/2003 |
| RU | 2248228 | 3/2005 |
| RU | 2525619 | 8/2014 |
| WO | WO 2009/089014 A1 | 7/2009 |
| WO | WO 2011/155089 | 12/2011 |
| WO | WO 2012/116407 | 9/2012 |
| WO | WO 2016/069090 | 5/2016 |
| WO | WO 2017/075359 | 5/2017 |
| WO | WO 2017/089887 | 6/2017 |
| WO | WO 2019/130311 | 7/2019 |

OTHER PUBLICATIONS

Grounds of Reason of Rejection Dated Aug. 28, 2023 From the Korean Intellectual Property Office Re. Application No. 10-2018-7017550 and Its Summary Into English. (11 Pages).
Machine Translation Dated Sep. 13, 2023 of Grounds of Reason of Rejection Dated Aug. 28, 2023 From the Korean Intellectual Property Office Re. Application No. 10-2018-7017550. (6 Pages).
Notification of Office Action and Search Report Dated Sep. 13, 2023 From the National Intellectual Property Administration of the People's Republic of China Re. Application No. 201880090395.5. (10 Pages).
Relatório de Exame Tecnico Dated Oct. 10, 2023 From the Serviço Público Federal, Ministério da Economia, Instituto Nacional da Propriedade Industrial do Brasil Re. Application No. BR 11 2018 010536 8 and Its Translation Into English. (6 Pages).
Grounds of Reason of Rejection Dated Nov. 16, 2023 From the Korean Intellectual Property Office Re. Application No. 10-2020-7021758 (8 Pages).
Machine Translation Dated Nov. 21, 2023 of Grounds of Reason of Rejection Dated Nov. 16, 2023 From the Korean Intellectual Property Office Re. Application No. 10-2020-7021758 (6 Pages).
Relatório de Exame Tecnico [Technical Examination Report] Dated May 23, 2023 From the Serviço Público Federal, Ministério da Economia, Instituto Nacional da Propriedade Industrial do Brasil Re. Application No. BR 11 2018 010536 8 and Its Translation Into English. (6 Pages).
Notice of Reason(s) for Rejection Dated Jun. 6, 2023 From the Japan Patent Office Re. Application No. 2020-535215 and Its Translation Into English. (5 Pages).
Official Action Dated May 4, 2023 from the US Patent and Trademark Office Re. U.S. Appl. No. 17/019,468. (34 pages).
Applicant-Initiated Interview Summary Dated Jan. 29, 2020 From the US Patent and Trademark Office Re. U.S. Appl. No. 15/778,707. (3 pages).
Communication Pursuant to Article 94(3) EPC Dated Oct. 7, 2021 From the European Patent Office Re. Application No. 16868090.8. (3 Pages).
Examination Report Dated Jun. 28, 2021 From the Australian Government, IP Australia Re. Application No. 2016359227. (2 Pages).
Examination Report Under Sections 12 & 13 of the Patents Act, 1970 and the Patents Rules, 2003 Dated May 17, 2021 From the Government of India, Intellectual Property India, Patents, Designs, Trade Marks, Geographical Indications, The Patent Office Re. Application No. 201837021589. 11 Pages).
Final Official Action Dated Mar. 4, 2022 from US Patent and Trademark Office Rc. U.S. Appl. No. 17/233,602. (37 pages).
Final Official Action Dated Apr. 21, 2020 from the US Patent and Trademark Office Re. U.S. Appl. No. 15/778,707. (24 pages).
International Preliminary Report on Patentability Dated Jun. 7, 2018 From the International Bureau of WIPO Re. Application No. PCT/IB2016/001731. (11 Pages).
International Search Report and the Written Opinion Dated May 18, 2017 From the International Searching Authority Re. Application No. PCT/IB2016/001731. (15 Pages).
Interview Summary Dated Oct. 8, 2021 From the US Patent and Trademark Office Re. U.S. Appl. No. 17/233,602. (2 Pages).
Notice of Allowance Dated Jul. 15, 2020 from the US Patent and Trademark Office Re. U.S. Appl. No. 15/778,707. (7 pages).
Notice of Allowance Dated Jul. 21, 2022 from US Patent and Trademark Office Re. U.S. Appl. No. 17/233,602. (9 pages).
Notice of Reason(s) for Rejection Dated Jan. 4, 2023 From the Japan Patent Office Re. Application No. 2020-535215 and Its Translation Into English. (20 Pages).
Notice of Reason(s) for Rejection Dated May 11, 2021 From the Japan Patent Office Re. Application No. 2018-525733 and Its Translation Into English.(6 Pages).
Notice of Reasons for Rejection Dated Oct. 27, 2020 From the Japan Patent Office Re. Application No. 2018-525733 and Its Translation Into English. (5 Pages).

(56) References Cited

OTHER PUBLICATIONS

Notification of Office Action Dated Jun. 18, 2021 From the State Intellectual Property Office of the People's Republic of China Re. Application No. 201680068609.X and Its Translation into English. (19 Pages).
Notification of Office Action and Search Report Dated Jan. 5, 2021 From the State Intellectual Property Office of the People's Republic of China Re. Application No. 201680068609.X and Its English Summary (18 Pages).
Office Action Dated Feb. 3, 2022 From the Israel Patent Office Re. Application No. 259474 and Its Translation Into English. (7 Pages).
Office Action Dated Apr. 12, 2021 From the Israel Patent Office Re. Application No. 259474 and Its Translation Into English. (6 Pages).
Official Action Dated Oct. 4, 2019 From the US Patent and Trademark Office Re. U.S. Appl. No. 15/778,707. (24 pages).
Official Action Dated Oct. 4, 2022 From the US Patent and Trademark Office Re. U.S. Appl. No. 17/019,468. (51 Pages).
Official Action Dated Nov. 17, 2021 from US Patent and Trademark Office Re. U.S. Appl. No. 17/233,602. (32 pages).
Official Action Dated Jul. 23, 2021 from the US Patent and Trademark Office Re. U.S. Appl. No. 17/233,602. (26 pages).
Patent Examination Report Dated Nov. 21, 2020 From the Australian Government, IP Australia Re. Application No. 2016359227. (5 Pages).
Requisition by the Examiner Dated Jan. 9, 2023 From the Innovation, Science and Economic Development Canada, Canadian Intellectual Property Office Rc. Application No. 3,004,513 and Claims. (14 pages).
Search Report and Opinion Dated Jul. 13, 2020 From the Servico Publico Federal, Ministerio da Economia, Instituto Nacional da Propriedade Industrial do Brasil Re. Application No. BR112018010536-8. (7 Pages).
Supplementary European Search Report and the European Search Opinion Dated Jul. 2, 2019 From the European Patent Office Re. Application No. 16868090.8. (6 Pages).
Examination Report Under Sections 12 & 13 of the Patents Act, 1970 and the Patents Rules, 2003 Dated Apr. 28, 2022 From the Government of India, Intellectual Property India, Patents, Designs, Trade Marks, Geographical Indications, The Patent Office Re. Application No. 202027032095 with Claims. (10 Pages).
Request for Examination and Search Report Dated Mar. 1, 2022 From the Federal Government Institution, Federal Institute of Industrial Property of the Federal Service of Intellectual Property, Patents and Trademarks of the Russian Federation, FIPS Re. 2020124618 and Its Translation Into English. (16 Pages).
Supplementary European Search Report and the European Search Opinion Dated Aug. 4, 2021 From the European Patent Office Re. Application No. 18895004.2. (6 Pages).
Zorba et al. "Autonomic Nervous System Dysfunction in Lifelong Premature Ejaculation: Analysis of Heart Rate Variability", Urology, 80(6):1283-1286, Dec. 2012.
International Preliminary Report on Patentability Dated Jul. 9, 2020 From the International Bureau of WIPO Re. Application No. PCT/IL2018/051402. (7 Pages).
International Search Report and the Written Opinion Dated Apr. 11, 2019 From the International Searching Authority Re. Application No. PCT/IL2018/051402. (10 Pages).
International Search Report and the Written Opinion Dated May 18, 2017 From the International Searching Authority Re. Application No. PCT/IB182016/001731. (17 Pages).
American Psychiatric Association Diagnostic and Statistical Manual of Mental Disorders DSM-5™, Association Psychiatric Association, 5th Ed., III: 1-947, 2013. (Part 1).
American Psychiatric Association Diagnostic and Statistical Manual of Mental Disorders DSM-5™, Association Psychiatric Association, 5th Ed., III: 1-947, 2013. (Part 2).
American Psychiatric Association Diagnostic and Statistical Manual of Mental Disorders DSM-5™, Association Psychiatric Association, 5th Ed., III: 1-947, 2013. (Part 3).
American Psychiatric Association Diagnostic and Statistical Manual of Mental Disorders DSM-5™, Association Psychiatric Association, 5th Ed., III: 1-947, 2013. (Part 4).
American Psychiatric Association Diagnostic and Statistical Manual of Mental Disorders DSM-5™, Association Psychiatric Association, 5th Ed., III: 1-947, 2013. (Part 5).
American Psychiatric Association Diagnostic and Statistical Manual of Mental Disorders DSM-5™, Association Psychiatric Association, 5th Ed., III: 1-947, 2013. (Part 6).
American Psychiatric Association Diagnostic and Statistical Manual of Mental Disorders DSM-5™, Association Psychiatric Association, 5th Ed., III: 1-947, 2013. (Part 7).
Case-Lo et al. "Delayed Ejaculation: Symptoms, Causes, Diagnosis, Treatment, Complications, Outlook, Diet and DE", HealthLine, 11 P., Jul. 21, 2016.
Donatucci "Etiology of Ejaculation and Pathophysiology of Premature Ejaculation", The Journal of Sexual Medicine, 3(Suppl.4): 303-308, Sep. 2006.
Doucet et al. "Neuromuscular Electrical Stimulation for Skeletal Muscle Function", Yale Journal of Biology and Medicine 85(2): 201-215, Jun. 2012.
Eisenberg et al. "Anogenital Distance as a Measure of Human Male Fertility", Journal of Assisted Reproduction and Genetics 32(3):479-484, Mar. 2015.
Eisenberg et al. "The Relationship Between Anogenital Distance and Age", Andrology, 1(1): 90-93, Jan. 2013.
Porter "Delayed Ejaculation DSM-5 302.74 (N53.11)", Theravive, Therapedia, 3 P., 2019.

\* cited by examiner

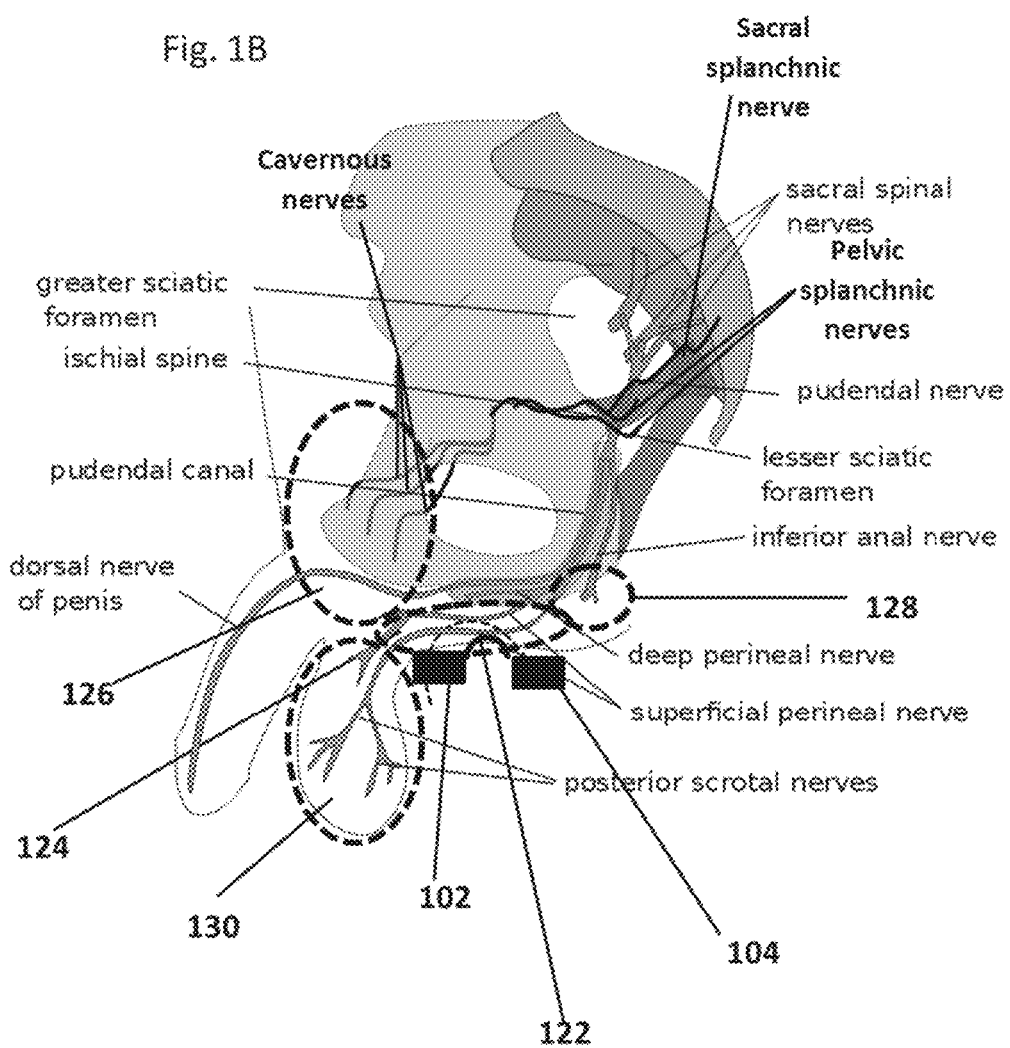

Fig. 2D
Fig. 2E
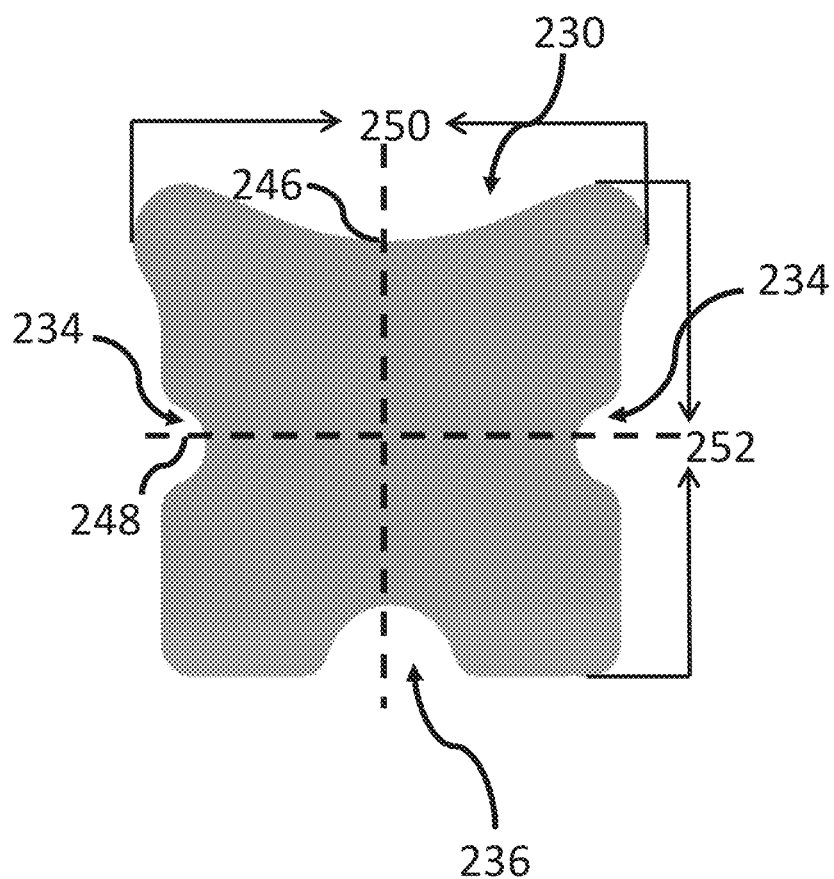
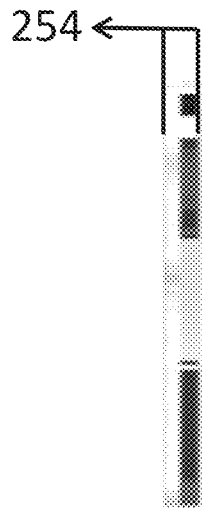

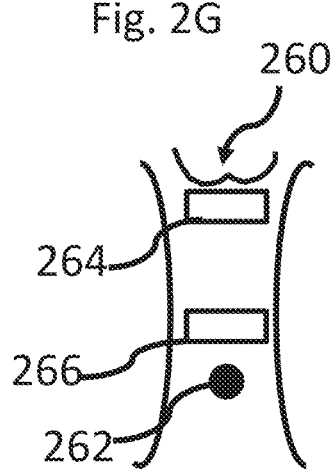
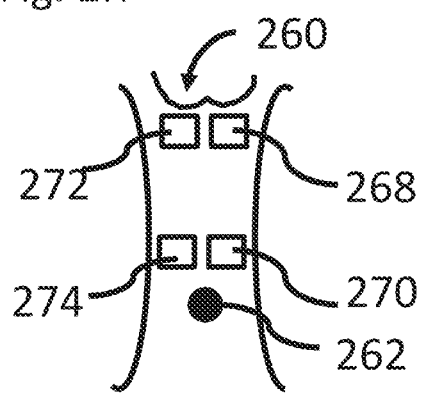
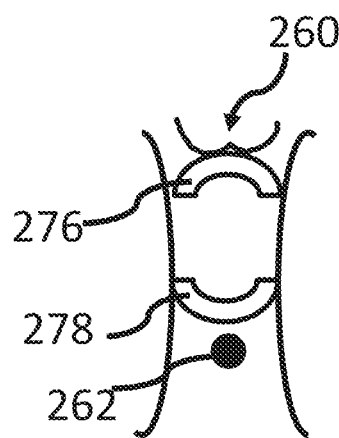
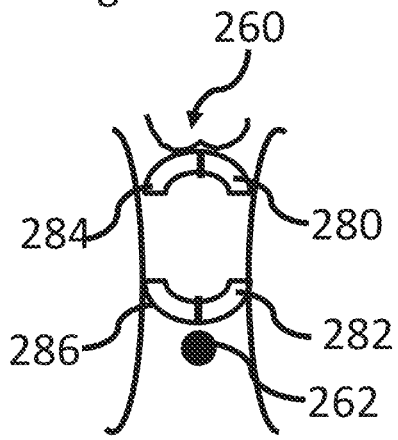
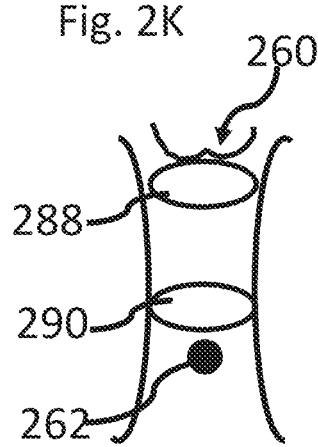
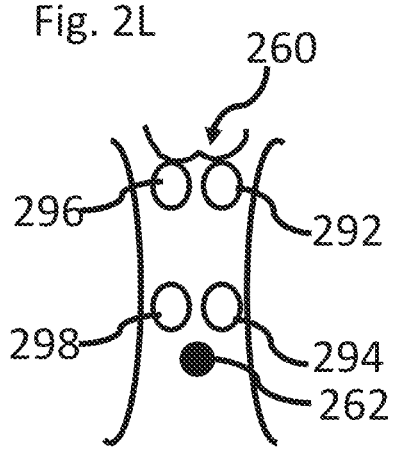

EJACULATION CONTROL

RELATED APPLICATIONS

This application is a continuation of U.S. patent application Ser. No. 16/957,752 filed on Jun. 25, 2020, now U.S. Pat. No. 12,017,067, issued on Jun. 25, 2024, which is a National Phase of PCT Patent Application No. PCT/IL2018/051402 having International Filing Date of Dec. 27, 2018, which claims the benefit of priority under 35 USC § 119 (e) of U.S. Provisional Patent Application No. 62/610,535 filed on Dec. 27, 2017.

PCT Patent Application No. PCT/IL2018/051402 is also related to PCT Patent Application No. PCT/IB2016/001731 filed on Nov. 17, 2016.

The contents of the above applications are all incorporated by reference as if fully set forth herein in their entirety.

FIELD AND BACKGROUND OF THE INVENTION

The present invention, in some embodiments thereof, relates to a device for electrifying nerves and/or muscles and, more particularly, but not exclusively, to a device and method for electrifying nerves and/or muscles of the perineum.

Ejaculation control is divided into three main conditions, premature ejaculation (PE), delayed ejaculation (DE), and retrograde ejaculation. PE is classified as a sexual disorder in the DSM-5 (Diagnostic and Statistical Manual of Mental Disorders, fifth edition). Its diagnosis is assigned to men who ejaculate prematurely during vaginal intercourse. PE can occur during other sexual activity, however it is only defined as a disorder in the case of vaginal intercourse, as a time duration for oral or manual stimulation has not been determined. Premature or early ejaculation is defined as the man feels unable to control their orgasm, and climaxes in less than one minute after vaginal penetration.

DE is also a DSM-5 sexual disorder in which a man is unable to ejaculate during sexual activity (American Psychiatric Association, 2013), specifically after 25 minutes to 30 minutes of continuous sexual stimulation (Case-lo, 2012; Nelson, 2012). This disorder is also known as DO (Delayed Orgasm) retarded ejaculation, or inhibited ejaculation (Nelson, 2012).

Retrograde ejaculation occurs when semen instead of being ejaculated through the urethra, is redirected to the urinary bladder.

Additional background art includes U.S. Pat. No. 5,562,717A, U.S. Patent Application Publication No. 2013/0116742 and U.S. Patent Application Publication No. 2015/0290450A1.

SUMMARY OF THE INVENTION

Some examples of some embodiments of the invention are listed below:

Example 1. A device for electrifying perineal tissue, comprising:
- a housing shaped and sized to be attached to a perineum surface of a subject between a posterior aspect of the scrotum and the anus of said subject;
- at least two electrodes in said housing configured to deliver an electric field to a perineal tissue, wherein said electrodes are positioned entirely between the scrotum and the anus of said subject;
- a pulse generator in said housing electrically connected to said at least two electrodes, wherein said pulse generator generates an electric field with parameter values selected to affect at least one selected target within said perineal tissue;
- a control circuitry in said housing electrically connected to said pulse generator;
- a readable and writable memory circuit in said housing electrically connected to said control circuitry, wherein said readable and writable memory stores indications of at least one electric field parameter and/or at least one treatment program.

Example 2. A device according to example 1, wherein a distance between the at least two electrodes is between 10 to 14 mm.

Example 3. A device according to examples 1 or 2, wherein said housing is thin and flexible enough to bend and conform to the anatomical curvature of the perineum.

Example 4. A device according to any one of the previous examples, comprising at least one thin battery in said housing electrically connected to said pulse generator.

Example 5. A device according to any one of the previous examples, comprising a communication circuitry in said housing electrically connected to said control circuitry, wherein said communication circuitry receives wireless signals from an external device, and wherein said control circuitry stores said received wireless signals in said memory and signals said pulse generator to generate said electric field based on said stored received wireless signals.

Example 6. A device according to example 5, wherein said external device comprises a mobile device and/or a wearable device.

Example 7. A device according to examples 5 or 6, wherein said communication circuitry transmits log files to said external device.

Example 8. A device according to any one of examples 5 to 7, wherein said communication circuitry signals said external device to generate a human detectable indication.

Example 9. A device according to example 8, wherein said device comprises at least one electrode or sensor for measuring impedance of the generated electric field, and wherein said communication circuitry signals said external device to generate said human detectable indication when values of said measured impedance are higher than 5000 ohm.

Example 10. A device according to example 9, wherein said control circuitry signals said pulse generator to stop generating said electric field if said measured impedance values are higher than 5000 ohm.

Example 11. A device according to example 9, wherein said device comprises at least one electrode or sensor for measuring values of at least one electrical parameter of the electric field, and wherein said control circuitry calculates impedance based on said measured values of said at least one electrical parameter of the electric field.

Example 12. A device according to example 11, wherein said communication circuitry signals said external device to generate said human detectable indication when values of said calculated impedance indicate an insufficient electrical contact between said at least two electrodes and said perineum surface.

Example 13. A device according to example 12, wherein said control circuitry signals said pulse generator to stop generating said electric field when values of said calculated impedance indicate an insufficient electrical contact between said at least two electrodes and said perineum surface.

Example 14. A device according to any one of the previous examples, wherein said housing comprises a proximal region with an inward curve shaped and sized to generally follow a posterior aspect of the scrotum and a distal region shaped and sized to be positioned near the anus.

Example 15. A device according to any one of the previous examples, wherein sad housing comprises at least one longitudinal bending line for bending the device to conform to the anatomical curvature of the perineum between the creases of the thighs.

Example 16. A device according to any one of the previous examples, wherein said housing comprises at least one transverse bending line for bending the device to conform to the anatomical curvature of the perineum between the posterior aspect of the scrotum and the anus.

Example 17. A device according to any one of the previous examples, wherein an axial length of said housing is shorter than the anogenital distance in said subject.

Example 18. A device according to example 17, wherein said axial length of said housing is in a range between 30-45 mm.

Example 19. A device according to any one of the previous examples, wherein a width of said housing is in a range between 35-55 mm.

Example 20. A device according to any one of the previous examples, wherein a thickness of said housing is in a range between 2-8 mm.

Example 21. A device according to any one of the previous examples, comprising at least one sensor or electrode electrically connected to said control circuitry for measuring values of at least one physiological parameter of said subject, and wherein said control circuitry signals said pulse generator to generate said electric field if said measured values are higher than a predetermined value stored in said memory and/or if said measured values are in a desired range of values stored in said memory.

Example 22. A device according to any one of the previous examples, wherein said at least one selected target comprises the Bulbospongiosus muscle and/or nerves innervating the Bulbospongiosus muscle.

Example 23. A device according to any one of the previous examples, wherein said at least one selected target comprises the Ischiocavernosus muscle and/or nerves innervating the Ischiocavernosus muscle.

Example 24. A device according to any one of the previous examples, wherein said electric field parameter comprises electric field frequency, and wherein said electric field frequency is at least 20 Hz.

Example 25. A device according to any one of the previous examples, wherein said electric field parameter comprises electric field intensity, and wherein said electric field intensity is at least 5 mA.

Example 26. A device according to any one of the previous examples, wherein said electric field parameter comprises interphase interval, and wherein said interphase interval is at least 30 μsec.

Example 27. A device according to any one of the previous examples, wherein said electric field parameter comprises pulse width, and wherein said pulse width is at least 200 μsec.

Example 28. A device for electrifying perineal tissue, comprising:
a housing attachable to the perineum skin;
at least two electrodes positioned in said housing of said device at a fixed distance between each other;
a pulse generator electrically connected to said at least two electrodes and configured to generate an electric field;
a control circuitry configured to signal said pulse generator to generate said electric field with parameter values suitable for interaction of said electric field with at least one selected target located at a depth of at least 5 mm from said perineum skin inside the perineal tissue when delivered through said at least two electrodes.

Example 29. A device according to example 28, wherein said at least one selected target comprises the Bulbospongiosus muscle and/or nerves innervating the Bulbospongiosus muscle.

Example 30. A device according to examples 28 or 29, wherein said at least one selected target comprises the Ischiocavernosus muscle and/or nerves innervating the Ischiocavernosus muscle.

Example 31. A device according to any one of examples 28 to 30, wherein a first electrode of said at least two electrodes is positioned on the perineum skin at a distance of at least 1 mm from the anus, and wherein a second electrode of said at least two electrodes is positioned on the perineum skin at a distance of up to 10 mm from the posterior aspect of the scrotum.

Example 32. A device according to any one of examples 28 to 31, wherein said at least two electrodes are positioned on the perineum skin at a distance of at least 10 mm between each other.

Example 33. A device according to any one of examples 28 to 32, wherein said at least two electrodes have a surface area of at least 400 mm$^2$.

Example 34. A device according to any one of examples 28 to 33, wherein at least one electrode of said at least two electrodes is rectangular.

Example 35. A device according to any one of examples 28 to 34, wherein at least one electrode of said at least two electrodes is circular or oval.

Example 36. A device according to any one of examples 28 to 35, wherein at least one electrode of said at least two electrodes is an arc subtending an angle of at least 30 degrees.

Example 37. A device according to any one of examples 28 to 36, wherein said at least two electrodes are attachable to the perineum surface between the anus and the posterior aspect of the scrotum.

Example 38. A device according to any one of examples 28 to 37, comprising at least one electrode array attachable to the perineum surface between the anus and the posterior aspect of the scrotum, and wherein at least one electrode of said at least two electrodes is part of said electrode array.

Example 39. A method for delivery an electric field to targets in perineal tissue comprising:
attaching a device configured to deliver an electric field to selected targets in perineal tissue to the perineum skin between a posterior aspect of the scrotum and the anus of said subject;
reading a value stored in a readable writable memory of said device;
generating said electric field by a pulse generator of said device based on said value;
delivering said electric field to said selected targets in perineal tissue by at least two electrodes of the device.

Example 40. The method of example 39, wherein said value comprises at a value of at least one electric field parameter and/or value of at least one treatment program stored in said readable writable memory.

Example 41. The method of examples 39 or 40, comprises wirelessly coupling said device to a mobile device configured to control said device by an application program installed in said mobile device, prior to said generating.

Example 42. The method of example 41, comprising signaling said coupled mobile device to generate a human detectable indication if said value of at least one electric field parameter is not within a desired range of values and/or is larger than a predetermined value.

Example 43. The method of examples 41 or 42, comprising receiving at least one wireless signal from said coupled mobile device.

Example 44. The method of example 43, comprising determining values of at least one parameter of said generated electric field and/or at least one parameter of a treatment program based on said at least one wireless signal of said receiving.

Example 45. The method of example 44, wherein said electric field parameter comprises intensity, voltage and/or frequency.

Example 46. The method of examples 44 or 45, wherein said treatment program parameter comprises interphase interval, pulse width and/or ramp time.

Example 47. The method of any one of examples 43 to 46, wherein said generating comprises generating said electric field in response to said at least one wireless signal of said receiving.

Example 48. The method of any one of examples 39 to 47, comprising measuring values at least one electrical parameter of the skin following said delivering.

Example 49. The method of example 48, comprising calculating impedance values based on said electrical parameter values of said measuring.

Example 50. The method of example 49, comprising stopping delivering of said electric field if said measured electrical parameter values and/or said impedance values are higher than a desired values or are not in a desired range of values.

Example 51. A method for targeting a selected region within the perineal tissue, comprising:
generating an electric field;
targeting a selected region located at a depth of at least 5 mm within the perineal tissue by delivering said electric field through at least two electrodes placed in contact with the perineum skin to said selected region.

Example 52. The method of example 51, wherein said generating comprises generating an electric field according to electric field parameters selected for targeting said selected region.

Example 53. The method of example 52, wherein said selected electric field parameters comprise electric field frequency and/or electric field intensity.

Example 54. The method of example 53, wherein said electric field intensity is at least 10 mA.

Example 55. The method of any one of examples 51 to 54, wherein said targeting comprises targeting said selected region by delivering said electric field through said at least two electrodes positioned at a fixed distance of at least 10 mm between each other and placed in contact with said perineum skin.

Example 56. The method of any one of examples 51 to 55, wherein said targeting comprises targeting said selected region by delivering said electric field through said at least two electrodes, wherein said at least two electrodes have a surface area of at least 400 mm$^2$.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as measuring electric field parameters, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A and 1B are schematic illustrations of electrodes attached to the perineum, according to some embodiments of the invention;

FIGS. 2D-2E are schematic illustrations of the device in an upper view (2D), and in a side view (2E), according to some embodiments of the invention;

FIGS. 2G-2L are schematic illustrations of electrodes, according to some embodiments of the invention;

DESCRIPTION OF SPECIFIC EMBODIMENTS OF THE INVENTION

Figure 1A:
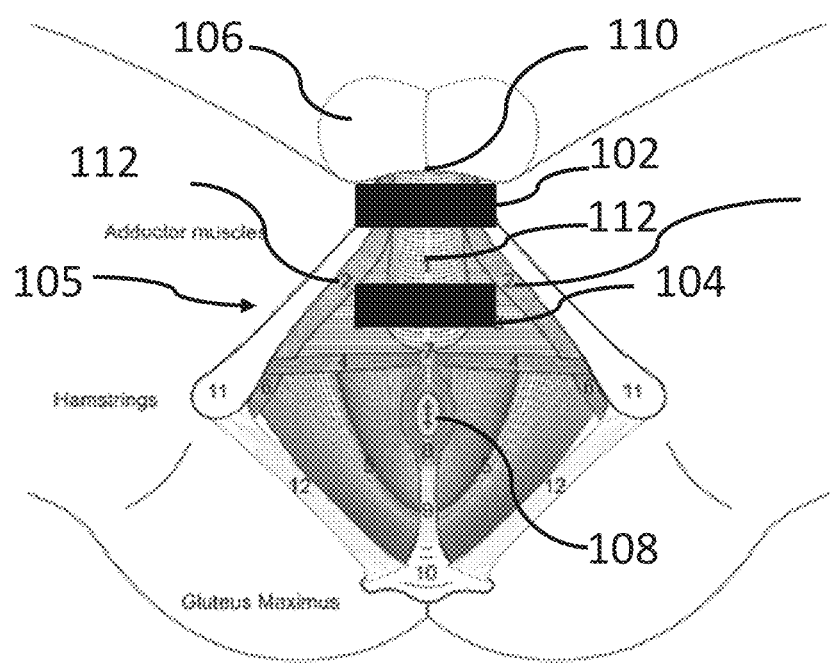

The present invention, in some embodiments thereof, relates to a device for electrifying nerves and/or muscles and, more particularly, but not exclusively, to a device and method for electrifying nerves and/or muscles of the perineum.

An aspect of some embodiments relates to selectively delivery of an electric field to at least one desired target in the perineal tissue of a subject. In some embodiments, the perineal tissue is a tissue located between the perineum skin the pelvic diagram, optionally up to a depth of 50 mm from the perineum skin. Additionally or optionally, the perineal tissue is defined as the tissue between the scrotum and the anus. In some embodiments, the electric field is directed to a desired target in the perineal tissue by positioning electrodes at selected locations, by using electrodes with selected shape and/or surface, and/or by adjusting the electric field parameters to reach the desired targets without causing pain or discomfort.

According to some embodiments, the electric field is directed to selected targets in the perineal tissue comprising the Bulbospongiosus muscle (formerly known as the Bulbocavernosus muscle) or nerves innervating Bulbospongiosus muscle, for example the motor branch of the pudendal nerve, and/or to the Ischiocavernosus muscle or nerves innervating the Ischiocavernosus muscle, for example the perineal branch of the pudendal nerve. Additionally or optionally, the electric field is delivered while reducing the electrification of undesired targets in the perineal tissue comprising (1) the Superficial Transverse Perineal muscle, innervated by the Perineal branch of the Pudendal nerve, (2) Levator Ani muscle, innervated by the Pudendal nerve, Perineal nerve and Inferior Rectal nerve, the (3) Cremaster muscle, innervated by the Genital Branch of the Genitofemoral nerve and, and/or the (4) External Anal Sphincter, innervated by the Perineal Branch of the Pudendal nerve and the Inferior Hemorrhoidal nerves. In some embodiments, the delivery of the electric field inhibits the rhythmic contractions of the bulbospongiosus muscle, which are typical to ejaculation. Alternatively, the electric field relaxes the bulbospongiosus muscle. A possible advantage of inhibiting those rhythmic contractions is that it may postpone ejaculation and prolong sexual intercourse. In some embodiments, the delivered electric field interacts, optionally directly interacts, with the muscles and/or nerved described above.

According to some embodiments, the electric field at a desired target is at least 25% larger than the electric field at an undesired target, for example 30% larger, 40% larger, 50% larger, 60% larger or any intermediate, smaller or larger value. In some embodiments, the electric field at an undesired target is at least 10% smaller than the electric field at the desired target, for example 10% smaller, 20% smaller, 30% smaller, 50% smaller or any intermediate, smaller or larger value.

According to some embodiments, the delivered electric field is used in the treatment of PE by interaction of the electric field with the muscles and/or nerves listed above. In some embodiments, the delivered electric field is used in the treatment of DE and/or retrograde ejaculation by interacting with the same muscles and/or nerves. Alternatively, the delivered electric field is used in the treatment of DE and/or retrograde ejaculation by interacting with other muscles and/or nerves located in the perineal tissue.

According to some embodiments, the delivered electric field is used in the treatment of erectile dysfunction (ED) disorders, optionally in combination with medications for the treatment of ED, for example Viagra®, Stendra, Cialis, Levitra and/or Staxyn. In some embodiments, the delivered electric field is used in the treatment of PE and ED. In some embodiments, patients that use the device for delivery of electric field to selected targets in the perineal tissue and also take medications, for example for the treatment of ED use a lower dose of the medications and/or different administration regime compared to subjects that do not use the device.

According to some embodiments, the electric field is delivered prior to and/or during the excitement phase of the sexual response cycle. Additionally or optionally, the electric field is delivered during the plateau phase and/or the orgasm phase and/or the resolution phase of the sexual response cycle. In some embodiments, the delivered electric field desensitizes nerves and/or muscles in the perineal tissue. In some embodiments, the desensitization of the muscles and/or nerves innervating the muscles leads to relaxation of the muscles. Alternatively or additionally, desensitization of nerves reduces pain sensation, for example pain sensation due to the delivered electric field. In some embodiments, the delivered electric field leads to ramp up of tension and/or contraction of muscles. In some embodiments, the electric field delivered to the selected targets in the perineal tissue prolongs the duration of the time from full erection to ejaculation, also termed the Ejaculatory Latency Time (ELT). In some embodiments, the delivered electric field prolongs ELT in at least 2 fold compared to the ELT duration without electric field delivery, for example 2 fold, 2.5 fold, 3 fold, 3.5 fold, 4 fold or any intermediate, smaller or larger increase ratio.

According to some embodiments the electric field is delivered by at least two electrodes that are shaped and sized to direct the electric field, optionally transcutaneous to the desired targets in the perineal tissue without causing a user to feel pain and/or discomfort. In some embodiments, the electrodes comprise rectangular electrodes, arc-shaped electrodes, oval or circular-shaped electrodes or any combination thereof. In some embodiments, the at least two electrodes differ in their surface area, for example one electrode has a larger surface area compared to the second electrode. Alternatively, the at least two electrodes have the same surface area. In some embodiments, the surface area is at least 100 $mm^2$, for example 100 $mm^2$, 200 $mm^2$, 400 $mm^2$, 450 $mm^2$, 500 $mm^2$ or any other intermediate smaller or larger surface area. In some embodiments, the distance between the at least two electrodes is adjusted to deliver the directed electric field. In some embodiments, the distance between the at least two electrodes is at least 8 mm, for example 10 mm, 11 mm, 12 mm, 13 mm, 14 mm or any intermediate or larger distance. In some embodiments, the distance between the at least two electrodes is in a range of 10 mm to 15 mm, for example 10 mm, 12 mm, 14 mm or any intermediate, smaller or larger value.

According to some embodiments, the electric field is directed to the desired target by selecting a pair of electrodes that are positioned at desired locations on the perineum skin. In some embodiments, the electrodes are positioned in different locations between the scrotum and the anus. Alternatively, one or more of the electrodes of the device are positioned near or adjacent to the anus, but are configured to deliver the electric field to a target tissue located away, for example at least 20 mm from the anus. In some embodiments, the position of the electrodes is selected when using an electrode array, and optionally pairing electrodes that are located at desired positions to deliver the electric field to the desired targets. In some embodiments, the selected pair of electrodes generates an electric field that can penetrate through the perineal tissue to the desired target.

According to some embodiments, at least one parameter of the electric field and/or at least one parameter of the treatment protocol are adjusted to allow delivery of the electric field to the desired targets. In some embodiments, the at least one parameter of the electric field comprises intensity, voltage and/or frequency of the electric field. In some embodiments, the at least one parameter of the treatment protocol comprises the duration of each electric field application, the number of electric field applications in each treatment session, the duration of each treatment session, interphase interval, pulse width and/or ramp time.

According to some embodiments, the electric field which is also termed herein as electric stimulation or stimulation, is delivered through the skin into the adjacent nerves and/or muscles, and causing the selected muscles to contract. Alternatively, the delivered electric field causes the selected muscle to relax. In some embodiments, the values of the electric field parameters are selected to allow efficient penetration of the electric field to the desired target without causing pain or discomfort. In some embodiments, the electric field parameters are selected to allow interaction with inner tissues of the perineum, for example inner muscles and inner nerves located at a depth of at least 5 mm inside the perineal tissue and optionally with minimal interaction with superficial tissues of the perineum, for example superficial nerves and/or superficial muscles located in a depth of 0-5 mm from the perineum skin. In some embodiments, the interaction of the electric field with the superficial tissues is less than 50% of the interaction with the inner tissues of the perineum.

According to some embodiments, the electric field parameter values are selected to allow penetration of the electric field into the perineal tissue to a depth in a range of 2 mm to 30 mm, for example 5 mm, 10 mm, 20 mm, 25 mm or any intermediate, smaller or larger value. In some embodiments, the electric field parameter values are selected to allow penetration of at least 2 mm from the perineum outer surface or the perineum skin and into the perineal tissue.

According to some embodiments, the intensity of the delivered stimulation or the intensity of the electric field is in a range of 0 mA (milli-amper) to 50 mA, for example 0 mA to 20 mA, 10 mA to 40 mA, 30 mA to 50 mA or any other intermediate range of values. In some embodiments, the intensity of the electric field delivered to the perineal tissue is in a range of 7 mA to 18 mA, for example 7 mA, 10 mA, 12 mA, 15 mA or any intermediate, smaller or larger value.

According to some embodiments, the frequency of the delivered stimulation or the frequency of the delivered electric field is in a range of 0 Hz (Hertz) to 100 Hz, for example 0 Hz to 50 Hz, 20 Hz to 60 Hz, 50 Hz to 100 Hz or any other intermediate range of values. In some embodiments, the electric field frequency is in a range of 20 Hz-50 Hz, for example 30 Hz, 35 Hz, 40 Hz or any intermediate smaller or larger value.

According to some embodiments, the electric field voltage is in a range of 50V (Volt) to 100V, for example 50V, 60V, 70V or any intermediate, smaller or larger value.

According to some embodiments, the interphase interval of the delivered stimulation or the delivered electric field is in a range of 0 usec (micro-seconds) to 30 usec, for example 0 usec to 10 μsec, 5 μsec to 20 μsec, 15 μsec to 30 μsec or any other intermediate range of values. In some embodiments, the interphase interval is in a range of 10 μsec to 100 μsec, for example 10 μsec, 60 μsec, 70 μsec, 80 μsec, 90 μsec or any intermediate, smaller or larger value.

According to some embodiments, the stimulation pulse width or the delivered electric field pulse width is in a range of 0 μsec to 800 μsec, for example 0 μsec to 300 μsec, 200 μsec to 600 μsec, 500 μsec to 800 μsec or any other intermediate range of values. In some embodiments, the electric field pulse width is in a range of 250 μsec to 350 μsec, for example 250 μsec, 300 μsec, 350 μsec or any intermediate, smaller or larger value.

According to some embodiments, the ramp time of the stimulation or the delivered electric field is in a range of 0 sec to 30 sec, for example 0 sec to 15 sec, 10 sec to 20 sec, 15 sec to 30 sec or any other intermediate range of values. In some embodiments, the ramp time of the delivered electric field is in a range of 5 sec to 10 sec, for example 5 sec, 7 sec, 9 sec or any intermediate, smaller or larger value.

According to some embodiments, the stimulation duration is predetermined as continuous or accumulated, for example for safety reasons. In some embodiments, the continuous stimulation duration is set to at least 1 minute, for example 7 minutes, 10 minutes, 12 minutes or any intermediate or larger value. Optionally, after reaching the maximal stimulation duration, the stimulation is turned off. In some embodiments, the accumulated stimulation duration is set to at least 1 minute, for example 7 minutes, 10 minutes, 12 minutes or any intermediate value, if the stimulation is paused and continued.

According to some embodiments, the stimulation duration is predetermined and preprogrammed into a control circuitry of the device. In some embodiments, the control circuitry executes a command to turn the stimulation off, for example, after 5 minutes, 7 minutes, 12 minutes or any other intermediate smaller or larger value. In some embodiments, a user determines the stimulation duration. Optionally, the device delivers an electric field for a maximal period of 19 minutes, for example 18 minutes, 15 minutes, 10 minutes or any intermediate or shorter duration. Optionally, the device delivers an electric field for a maximal duration of 10 minutes.

According to some embodiments, the device is preprogrammed to stimulate at a certain intensity value, without the need of a software application controlling the device, for example an app, installed in a smartphone, a tablet or a smartwatch. In some embodiments, this intensity value may be 10 mA, 15 mA, 20 mA or any intermediate, smaller or larger value.

According to some embodiments, the electric field is delivered to a depth between 25-50 mm inside the perineal tissue, for example into the sub-perineal tissue. In some embodiments, the electric field is delivered into the sub-perineal tissue without causing pain to a subject. In some embodiments, the electric field delivered to the sub-perineal tissue has a reduced effect on the skin of the perineum, for example on the foreskin and/or on the superficial perineal fascia. In some embodiments, the reduced effect is lower than the threshold of pain sensation in the skin of the perineum and/or in the superficial perineal fascia.

An aspect of some embodiments, relates to delivery of an electric field to the perineal tissue by a flexible device sized and shaped to be entirely attached to the outer surface of the perineum between the scrotum and the anus of a subject. In some embodiments, the electric field is generated based on programs and/or values of at least one electric field parameter stored in a readable and writable memory of the device.

According to some embodiments, the device is at least partly bendable, for example to conform to the anatomical curvature of the perineum. Alternatively or additionally, the device is at least partially bendable to conform to anatomical changes during sexual intercourse, for example anatomical changes in the perineum region during sexual intercourse. In some embodiments, the device housing comprise at least two axial bending lines, for example to direct the bending the device. Alternatively or additionally, the device comprises a flexible printed circuit board (fPCB) with cuts, for example to allow bending of the fPCB.

According to some embodiments, the device is shaped to allow accurate axial orientation and to reduce positioning errors when attaching the device to the perineum. In some embodiments, the device proximal region has a concave shape, for example to allow easy orientation and attachment of the device to the posterior aspect of the scrotum.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Perineal Tissue Electrification

Reference is now made to FIGS. 1A and 1B depicting at least two electrodes attached to the perineum outer surface, according to some exemplary embodiments of the invention. According to some exemplary embodiments, the electrodes, for example electrodes 102 and 104 are placed in contact with the outer surface of the perineum 105. In some embodiments the electrodes are positioned between the posterior aspect 110 of the scrotum 106 and the anus 108. In some embodiments, an anterior electrode, for example electrode 102 is positioned adjacent to the posterior aspect 110 of the scrotum 106, for example at a distance of 0.5 mm, 1 mm, 1.5 mm or any intermediate, smaller or larger distance from the scrotum. In some embodiments, the posterior electrode, for example electrode 104, is positioned at a distance of at least 1 mm away from the anus 108. In some embodiments, positioning the posterior electrode too close to the anus 108 may cause discomfort and anal contraction upon electric field delivery.

According to some exemplary embodiments, the electrodes for example electrodes 102 and 104 are positioned at a desired distance between each other on the outer surface of the perineum, to direct an electric field 122 to selected regions in the perineal tissue, for example region 124. In some embodiments region 124 comprise the Bulbospongiosus (formerly known as the Bulbocavernosus) and Ischiocavernosus muscles, and their innervating nerves, the motor branch of the pudendal nerve and perineal branch of the pudendal nerve, respectively. In some embodiments, the position of the electrodes allows to direct the electric field 122 away from undesired regions, for example regions 126, 128 and 130. In some embodiments, the undesired regions comprise, the Superficial Transverse Perineal muscle, innervated by the Perineal branch of the Pudendal nerve, the Levator Ani muscle, innervated by the Pudendal nerve, the Perineal nerve and the Inferior Rectal nerve, the Cremaster muscle, innervated by the Genital Branch of the Genitofemoral nerve and, the External Anal Sphincter, innervated by the Perineal Branch of the Pudendal nerve and the Inferior Hemorrhoidal nerves.

Exemplary Device

According to some embodiments, a device for the delivery of an electric field to the perineal tissue is attached entirely between the anus and the posterior aspect of the scrotum. In some embodiments, the device does not have any wires outside of the device housing, for example to reduce discomfort and/or to simplify device attachment.

Figure 2A:
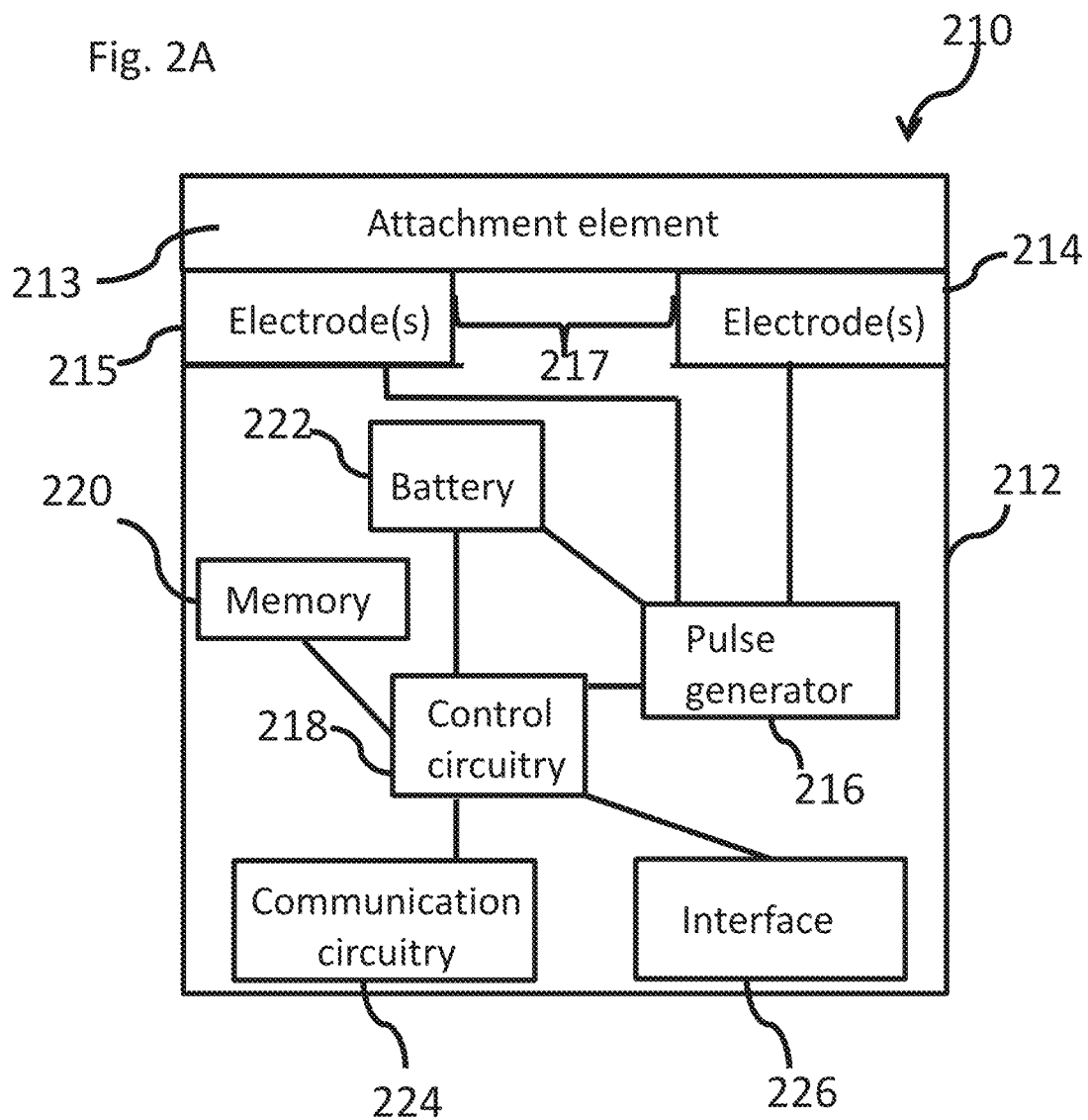
FIG. 2A is a block diagram of a device for electrifying perineal tissue, according to some embodiments of the invention.

Reference is now made to FIG. 2A, depicting the device components, according to some exemplary embodiments of the invention. According to some exemplary embodiments, device 210 comprises a thin housing 212 having an upper flat face and a lower face. In some embodiments, the width of the housing is between 1 mm and 10 mm, for example 1 mm, 2 mm, 3 mm, 4 mm, 5 mm, 7 mm, 9 mm, 10 mm or any intermediate width. In some embodiments, the device and the housing 212 are shaped and sized to be positioned entirely between the posterior aspect of the scrotum and the anus.

Additionally, the axial length of the device and the housing is shorter than the anogenital distance. In some embodiments, the housing comprises axial bending lines, for example to direct the bending of the housing to conform to the anatomical curvature of the perineum, and to allow, for example to attach the device and the housing of the device between the left and right creases of the thighs. In some embodiments, the housing 212 comprises an attachment element 213 for attaching the upper flat face of the housing 212 to the outer surface of the perineum. In some embodiments, the attachment element comprises a sticker with glue, optionally a reusable sticker which allows for example to remove and re-attach the device to the perineum outer surface several times. In some embodiments, the attachment element 213, optionally at the interface between the device and the skin comprises a conductive and optionally an adhesive hydrogel, for example to allow better conductance when attaching the device to a hairy perineal skin.

According to some exemplary embodiments, the device comprises at least two electrodes, for example electrodes 214 and electrodes 215 positioned at least partly on the upper face of the housing 212. Alternatively, the at least two electrodes are positioned inside the housing, and deliver the electric field through a conductive layer positioned on top of the housing. In some embodiments, the electrodes are positioned along the anogenital distance and/or in parallel to each other. In some embodiments, the electrodes comprise 2, 3, 4, 5, 6 electrodes or any smaller or larger number of electrodes.

In some embodiments, at least some of the electrodes are unipolar.

Optionally some of the electrodes are bipolar. In some embodiments, the electrodes comprise at least one sensing electrode positioned at the upper face of the housing, for example to measure at least one physiological parameter of the body, for example heart rate and/or electrical conductivity of one or more muscles. In some embodiments, the electrodes, for example electrodes 214 and/or electrodes 215 have a surface area in a range between 90 $mm^2$ and 850 $mm^2$, for example 100 $mm^2$, 200 $mm^2$, 300 $mm^2$, 400 $mm^2$ or any intermediate, larger or smaller value. In some embodiments, using electrodes with a surface area smaller than 90 $mm^2$ may yield large current and power density which may cause pain and discomfort to the user. In some embodiments, using electrodes with surface area larger than 850 mm² may result with large current distribution and inefficient stimulation. According to some exemplary embodiments, the electrodes for example electrodes 214 and electrodes 215 are positioned at a distance of at least 8 mm between each other, for example 10 mm, 11 mm, 12 mm, 13 mm, 14 mm or any intermediate or larger distance.

According to some exemplary embodiments, the device 210 comprises a pulse generator positioned inside the housing 212. In some embodiments, the pulse generator is electrically connected to at least some of the electrodes 214. In some embodiments, a control circuitry, for example control circuitry 218 is electrically connected to the pulse generator 216. In some embodiments, the control circuitry 218 signals the pulse generator 216 to generate an electric field according to at least one protocol and/or according to electric field parameter values stored in a memory 220, which is optionally a readable and writable memory. In some embodiments, the electric field parameters comprise intensity, voltage, frequency, interphase interval, pulse width and/or ramp time.

According to some exemplary embodiments, the device 210 comprises an interface 226, for example for receiving input from a user and/or for delivery of indications to the user. In some embodiments, the interface comprises at least one light source, for example a light emitting diode (LED) and/or at least one sound producing element. In some embodiments, the interface 226 delivers indications related to the treatment protocol and/or the electric field. Alternatively or additionally, the interface 226 delivered indications related to the status of the device 210, for example when the device is turned on, when the device delivers an electric field, and/or when the device is in a non-stimulating mode. In some embodiments, the interface delivers alerts to a user, for example a low battery alert and/or alerts related to device malfunctioning.

According to some exemplary embodiments, the device 210 comprises a communication circuitry 224 electrically connected to the control circuitry 218 inside the housing 212. In some embodiments, the communication circuitry receives and/or transmits wireless signals, for example Bluetooth signals, WiFi or any other wireless signals. In some embodiments, the control circuitry comprises a receiver, for example for receiving the wireless signals from a remote device, for example a wearable device or a mobile device. Optionally, the receiver receives the wireless signals from a computer. In some embodiments, the communication circuitry comprises a transmitter, for example for transmitting the wireless signals to a remote device, for example a wearable device or a mobile device. Optionally, the transmitter transmits the wireless signals to computer.

According to some exemplary embodiments, the device 210 comprises at least one battery, for example battery 222 inside the housing 212. In some embodiments the battery 222 is a rechargeable battery, for example a lithium ion battery. In some embodiments, the battery 222 is remotely charged. Alternatively, the battery 222 is a non-rechargeable battery. Optionally, the battery is a thin battery, for example a coin or a disc shaped battery. In some embodiments, the battery 222 is a replaceable battery, for example a battery that can be replaced by the removal of a cover in the housing 212.

According to some exemplary embodiments, the device 210 measures and/or calculates at least one electrical parameter of the skin, for example impedance. In some embodiments, the electrical parameter of the skin is measured by at least one electrode or at least one sensor of the device which is in an electrical contact with the skin. In some embodiments, the electrical impedance monitoring is used to determine the quality of adhesion of the device to the skin, prior to the delivery of the electric field and/or during the delivery of the electric field. In some embodiments, high impedance values, for example impedance values of at least 5000 ohm, for example 5000 ohm, 6000 ohm, 7000 ohm or any intermediate or larger value indicates that the device has no contact with the skin.

In some embodiments, in this case, the device would automatically cease stimulation and optionally signals a mobile device, for example a smartphone to deliver an alert to the user. In some embodiments, gradually decreasing impedance values, for example at a rate of at least 50 ohm per second, for example 50 ohm per second, 100 ohm per second, 500 ohm per second or any intermediate or larger rate may indicate of nerve activity which may indicate of approaching ejaculation and/or urination.

According to some exemplary embodiments, low impedance values, for example impedance values of 1000 ohm and lower, for example 900 ohm, 800 ohm, 700 ohm or any intermediate or smaller value would indicate that the device is properly contacting the skin. In some embodiments, in this case, the device would signal the smartphone to deliver an indication to the user that the device is properly attached to the skin.

According to some exemplary embodiments, measured impedance values in a range between 1000 ohm and 5000 ohm indicates that the device is sub-optimally applied to the skin. In some embodiments, in this case, the device would signal the smartphone to generate a warning indication to the user.

According to some embodiments, if the measured or calculated impedance values indicate an insufficient contact between electrodes of the device and the perineum surface or perineum skin, the device stops generation of the electric field and/or delivers an indication to a user. Optionally, the indication to the user is delivered by a mobile device wirelessly coupled to the device.

Exemplary Device Design

Figure 2B:
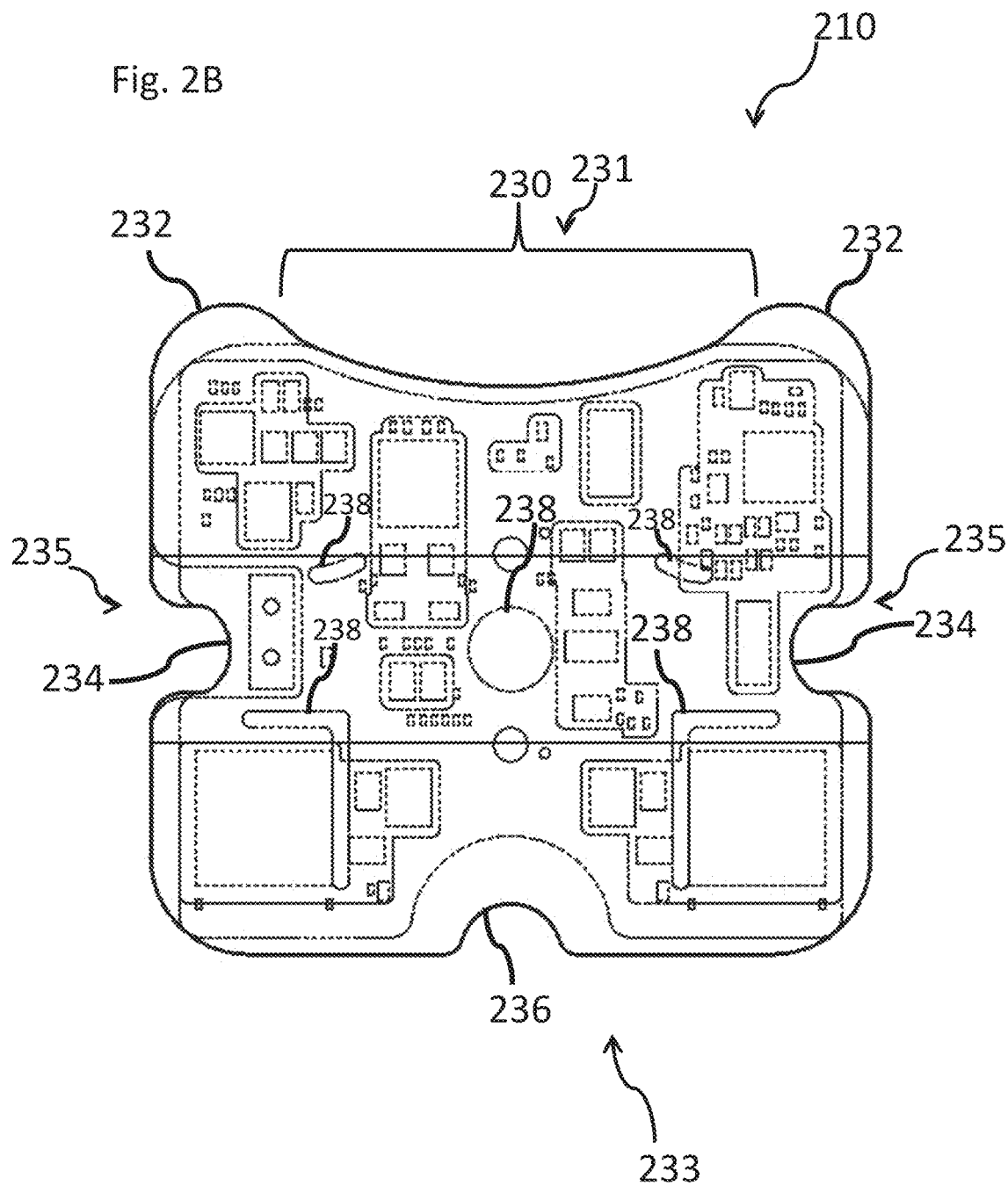
FIG. 2B is a schematic illustration of the device outer surface and electrical circuit, according to some embodiments of the invention.

According to some exemplary embodiments, the device is shaped and sized to be positioned between the scrotum and the anus, and to be flexible enough to bend according to the anatomical curves of the perineum. Reference is now made to FIG. 2B depicting the device design, according to some exemplary embodiments of the invention.

According to some exemplary embodiments, the device housing has an inward notch, for example an inward arch cut 230 in the proximal region 231 of the device 210, for example to easily fit and attach the device to the posterior aspect of a subject scrotum. In some embodiments, the inward arch cut 230 is according to a cut in a PCB inner layer of the device 210. In some embodiments, the inward notch has a width in a range of 10-45 mm, for example 10 mm, 15 mm, 30 mm, 40 mm or any intermediate, smaller or larger value. In some embodiments, on both sides of the inward curve 230, the device 210 comprises two removal grasp tips 232, one on each side of the inward curve 230. In some embodiments, the device 210 comprises two lateral notches, for example curve cuts 234, one cut on each side of the device 210, for example to allow easy torsion of the device 210. In some embodiments, device 210 comprises at least one distal notch, for example distal cut 236 in the distal region 233 of the device 210. Optionally, the arch cut 236 conforms to the shape and/or position of the anus, for example to allow the accurate positioning of the device 210 without covering the anus. In some embodiments, positioning the device in a distance from the anus and the proximal tissue surrounding the anus will allow for example to avoid undesired stimulation of the External Anal Sphincter and innervations.

Figure 2C:
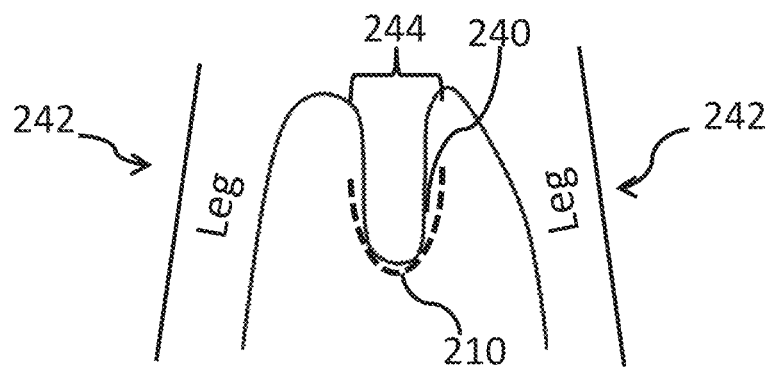
FIG. 2C is a schematic illustration of the device attached to the perineum, according to some embodiments of the invention.

Reference is now made to FIG. 2C depicting the bending of the device to fit the anatomical curvature in the perineum region, according to some exemplary embodiments of the invention. FIG. 2C shows an exaggerated representation of the perineum 240. According to some exemplary embodiments, the device 210 is bent is attached to the outer surface of the perineum 240, for example to the skin of the perineum 240, and is bent to conform to the anatomical curves of the perineum 240 between the two legs 242. In some embodiments, the device is bent along the scrotum-anus axis until the distance 244 between the lateral sides of the device 210 is minimum 5 mm, for example 5 mm, 5.5 mm, 6 mm or any intermediate or larger distance.

Reference is now made to FIGS. 2D and 2E depicting the device external design and dimensions, according to some exemplary embodiments of the invention.

According to some exemplary embodiments, the device comprises at least one longitudinal bending line, for example a longitudinal bending line 246 which optionally passes through the inward curve 230 and the distal cut 236. In some embodiments, the device comprises at least one transverse bending line, for example transverse bending line 248, which optionally passes through the lateral curve cuts 234.

According to some exemplary embodiments of the invention, the device length, for example length 252 is in a range of 25-45 mm, for example 25 mm, 30 mm, 36, 40 mm or any intermediate smaller or larger value. In some embodiments, the device length 252 is shorter than the anogenital distance between the posterior aspect of the scrotum and the anus.

According to some exemplary embodiments, the device and/or housing width, for example width 250 is in a range of 32-52 mm, for example 32 mm, 35 mm, 40 mm, 42 mm, 45 mm or any intermediate smaller or larger value. In some embodiments, the device width is smaller than the distance between the creases of the left and right thighs.

According to some exemplary embodiments, the device thickness, for example thickness 254 is in a range of 1-10 mm, for example 1 mm, 2 mm, 4 mm, 5 mm, 7 mm or any intermediate smaller or larger value. In some embodiments, the thickness is designed to be as minimal as possible, for example to avoid any discomfort and/or pain when the device is attached to the perineum skin during sexual intercourse.

Figure 2F:
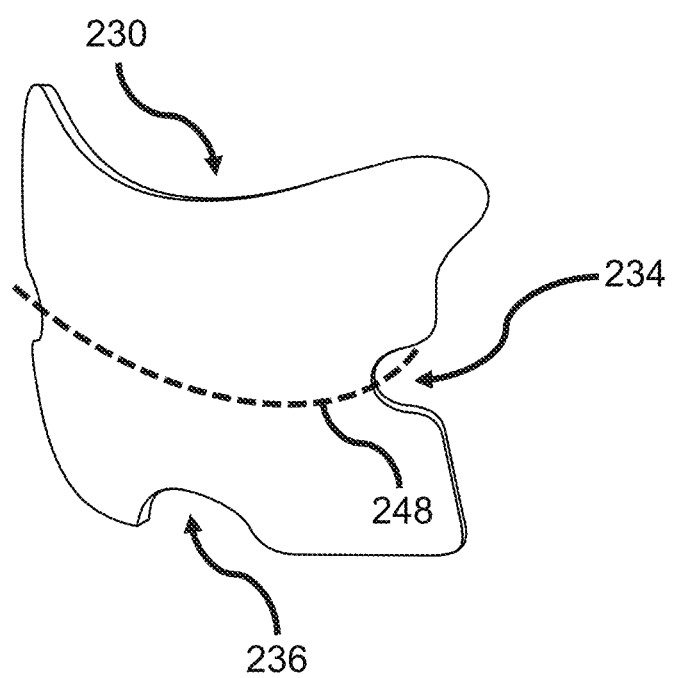
FIG. 2F is a schematic illustration of the device where the device is bent along a longitudinal axis, according to some embodiments of the invention.

Reference is now made to FIG. 2F depicting bending of the device, according to some exemplary embodiments of the invention. According to some exemplary embodiments, the device is bent along the transverse bending line 248, for example to conform to the perineum anatomical curvature between the creases of the left and right thighs. Additionally or optionally, the device is bent along the longitudinal bending line 250, for example to conform to the perineum anatomical curvature between the posterior aspect of the scrotum and the anus.

Exemplary Electrodes

According to some exemplary embodiments, the device, for example device 210 delivers a directed electric field to selected targets in the perineal tissue. In some embodiments, the electrodes of the device are shaped and/or are spatially arranged for directing the electric field.

Reference is now made to FIGS. 2G-2L, depicting different spatial rearrangements and/or shapes of the electrodes on the upper surface of the device housing which faces the perineum skin.

According to some exemplary embodiments, the electrodes comprise at least two electrodes positioned between the scrotum and the anus. In some embodiments, for example as shown in FIG. 2G, the electrodes comprise a proximal electrode 264 positioned near the scrotum 260, and a distal electrode 266 positioned at a distance from the anus 262. In some embodiments, the proximal electrode and/or the distal electrode 266 are shaped as rectangles. In some embodiments, for example as shown in FIG. 2H the device comprises at least two proximal electrodes 268 and 272 positioned near the scrotum 260, and at least two distal electrodes 270 and 274 positioned at a distance from the anus 262. In some embodiments, the at least two proximal electrodes and/or the at least two distal electrodes are shaped as rectangles.

According to some exemplary embodiments, for example as shown in FIG. 2I, the device comprises at least two arc-shaped electrodes 276 and 278. In some embodiments, the electrodes 276 and 278 are shaped as an arc subtending an angle between 0-270 degrees, for example 10 degrees, 20 degrees, 30 degrees, 45 degrees, 90 degrees, 180 degrees or any intermediate smaller or larger angle. In some embodiments, a proximal arc electrode 276 is positioned near the scrotum 260 and the distal arc 278 is positioned in a distance from the anus 262. In some embodiments, for example as shown in FIG. 2J, the device comprises at least two proximal arc-shaped electrodes 280 and 284 positioned near the scrotum 260, and at least two distal arc-shaped electrodes 282 and 286 positioned in a distance from the anus 262.

In some embodiments, at least some of the at least two proximal electrodes 280 and 284 and the at least two distal electrodes 282 and 286 are shaped as an arc subtending an angle between 0-180 degrees. In some embodiments, the convex face of arc-shaped electrode 276 or arc shaped electrodes 280 and 284 faces the scrotum and/or the convex face of arc shaped electrode 278 or electrodes 282 and 286 faces the anus. In some embodiments, the concave face of arc-shaped electrode 276 or electrodes 280 and 284 faces the scrotum and/or the concave face of arc-shaped electrode 278 or electrodes 280 and 284 faces the anus.

According to some exemplary embodiments, for example as shown in FIG. 2K, the device comprises at least two round electrodes 288 and 290. In some embodiments, the at least two round electrodes are shaped as a circle or as an ellipse. In some embodiments, the round or circular electrodes have a diameter in the range of 5-60 mm, for example 10 mm, 20 mm, 30 mm, 40 mm or any intermediate smaller or larger diameter. In some embodiments, the proximal round electrode 288 is positioned near the scrotum 260 and the distal round electrode is positioned in a distance from the anus 262.

In some embodiments, for example as shown in FIG. 2L, the device comprises at least two round-shaped proximal electrodes 292 and 296, and at least two round-shaped distal electrodes 294 and 298. In some embodiments, the at least two round shaped proximal electrodes are positioned near the scrotum 260, and the at least two round shaped distal electrodes 294 and 298 are positioned at a distance from the anus 262. In some embodiments, the minimal distance between the two proximal electrodes, for example electrodes 292 and 296, electrodes 284 and 280, or electrodes 268 and 272 is at least 1 mm, for example 1 mm, 1.5 mm, 1.7 mm or any intermediate or larger distance. In some embodiments, the minimal distance between the two distal electrodes, for example electrodes 294 and 298, electrodes 282 and 286, or electrodes 270 and 274 is at least 1 mm, for example 1 mm, 1.5 mm, 1.7 mm or any intermediate or larger distance.

Figure 2M:
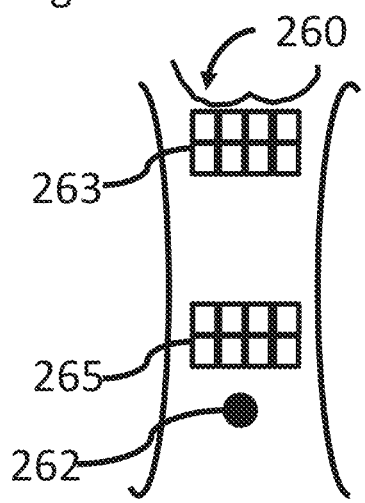
FIGS. 2M-2N are schematic illustrations of electrode array, according to some embodiments of the invention.
Figure 2N:
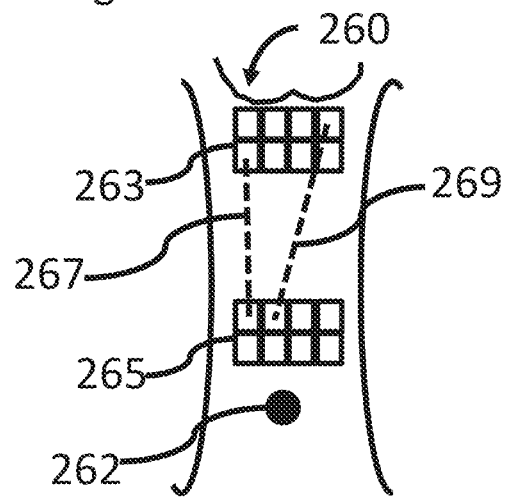

Reference is now made to FIGS. 2M and 2N depicting electrodes arranged in electrode arrays, according to some exemplary embodiments of the invention.

According to some exemplary embodiments, at least one electrode array, for example electrode array 263 is positioned near the scrotum 260 and/or at least one electrode array, for example electrode array 265 is positioned near or at a distance from the anus 262. In some embodiments, for example as shown in FIG. 2N, at least one pair of electrodes, one electrode from electrode array 263 and one from electrode array 265 is selected, for example to provide a directed electric field to selected targets in the perineal tissue.

Exemplary Device Connectivity

Figure 3:
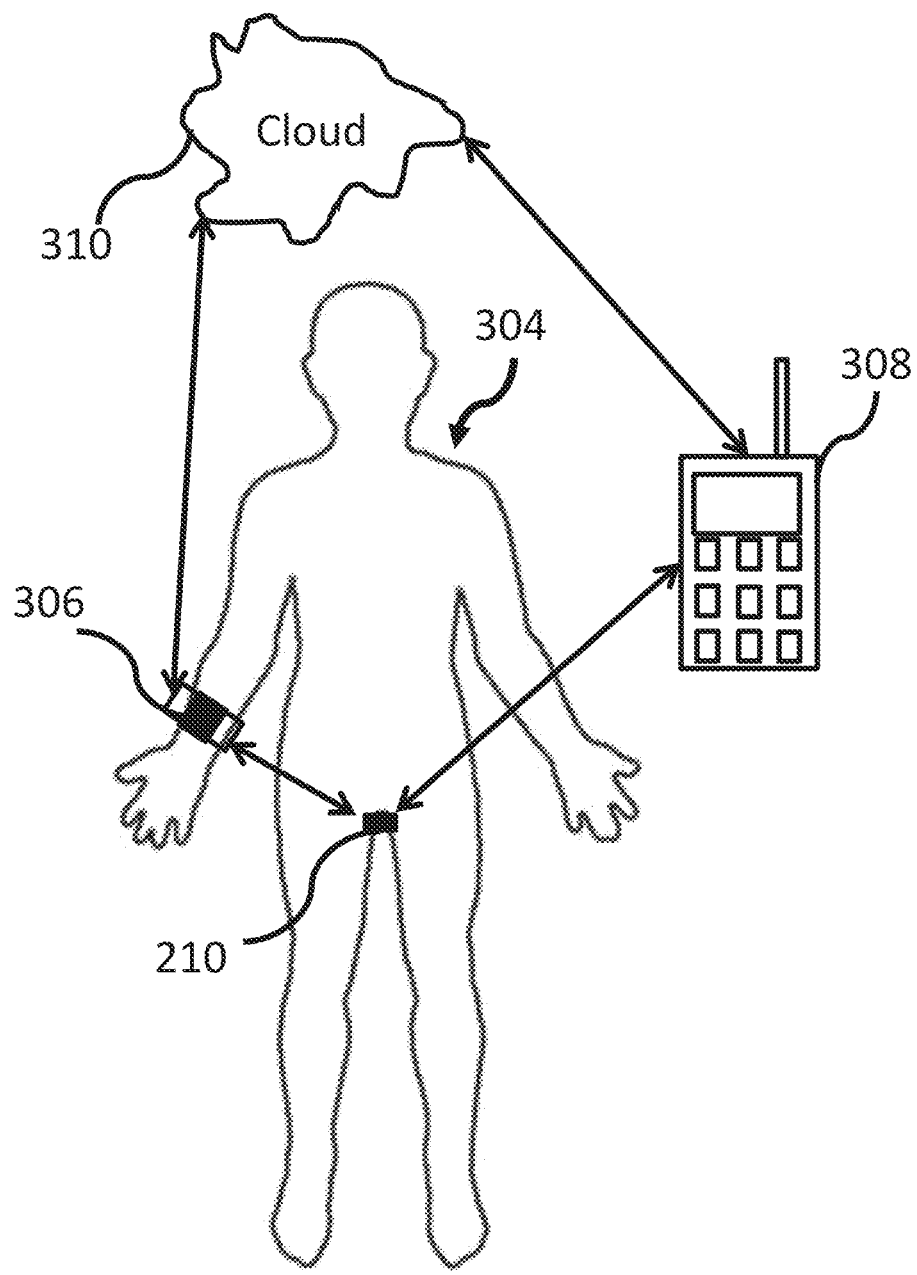
FIG. 3 is a schematic illustration of the device connections to external devices, according to some embodiments of the invention.

According to some exemplary embodiments, the device receives and/or transmits wireless signals to remote devices. Reference is now made to FIG. 3 depicting the connectivity of a device, for example device 210 attached to the perineum of a subject 304, according to some exemplary embodiments of the invention.

According to some exemplary embodiments, the device 210 communicated by wireless signals, for example Bluetooth and/or WiFi s signals with remote device. In some embodiments, the device 210 communicates with a wearable device 306, for example a smartwatch or a fitness bracelet. Alternatively or additionally, the device 210 communicates with a mobile device 308, for example a smartphone or any other mobile device. In some embodiments, a software application or a software program installed in a memory of the wearable device 306 and/or the mobile device 308 controls and/or monitors the operation of the device 210.

According to some exemplary embodiments, the device 210 is under a control and/or in communication with a device which comprises one or more microphones and a remote virtual assistant stored in a memory of the device, for example Alexa™ by Amazon™. Alternatively or additionally, the remote virtual assistant is stored in a remote memory cloud. In some embodiments, the virtual assistant activates and/or controls the activation of the device 210. In some embodiments, the virtual assistant controls the activation of the device 210 according to values of one or more parameters stored in a remote memory storage, for example a memory cloud, in communication with the virtual assistant. Alternatively or additionally, the virtual assistant receives data, for example activation log files of the device 210 and/or one or more clinical parameters. Optionally, the virtual assistant stores the data in the memory cloud.

According to some exemplary embodiments, the remote virtual assistant analyzes audio signals, for example sound, received by the one or more microphones. Optionally, the audio signals comprise voices of a user of the device 210 and/or voices of the user's partner before, during and/or after intercourse. In some embodiments, the audio signals comprise background sounds, for example sounds generated by clothes, and/or shoes.

According to some exemplary embodiments, the remote virtual assistant controls the activation, for example activates and/or deactivates the device 210 according to the analyzed audio signals. In some embodiments, the remote virtual assistant activates the device when sounds of clothes removal are identified. In some embodiments, the remote virtual assistant controls the activation of the device 210 based on audio signals received during intercourse. In some embodiments, the remote virtual assistant identifies stages in the intercourse based on the received audio signals and modifies the activation of the device 210 accordingly, for example when specific audio signals are received the remote virtual assistant stops the pulse generation by the device 210 to allow ejaculation According to some exemplary embodiments, the device 210 is voice activated, for example based on voice commands received by a microphone within the device 210 and/or based on voices commands received by an external microphone, for example the remote virtual assistant-associated microphone. Optionally, the device 210 and/or the virtual assistant identify a pre-determined voice pattern, for example a voice pattern of a user and/or a voice pattern of a user partner. In some embodiments, the device 210 is activated or the activation of the device 210 is controlled only in response to voice commands of a one or more pre-determined voice patterns, for example personalized voice patterns.

In some embodiments, the software application or the software program allow to modify at least one parameter of the delivered electric field, for example intensity, voltage, frequency, pulse width and/or at least one treatment parameter, for example timing of the treatment, interphase interval, ramp time. In some embodiments, the device 210 receives measured values of at least one physiological parameter, for example heart rate from the wearable device 306 by wireless signals.

According to some exemplary embodiments, the device 210 is in communication with an information storage cloud, for example cloud 310 by the wireless signals. In some embodiments, the device 210 receives from the cloud 310 values of at least one electric field parameter and/or values of at least one treatment parameter. In some embodiments, the device 210 transmits to the cloud 310 and/or to the wearable device 306 or mobile device 308 log files and/or measured values of at least one physiological parameter, for example heart rate or electrical activity of perineal muscles.

Optionally, the cloud comprises at least one table and/or at least one algorithm that modifies at least one parameter of the delivered electric field based on the information received from the device 210. In some embodiments, the cloud 310 then delivered the modified parameter values to the device 210. In some embodiments, software applications or programs installed in the wearable device 306 and/or the mobile device 308 comprise at least one table and/or at least one algorithm. In some embodiments, the wearable device 306 and/or the mobile device 306 modify values of at least one electric field parameter values based on the information received from the device 210.

Exemplary Device Activation

Figure 4A:
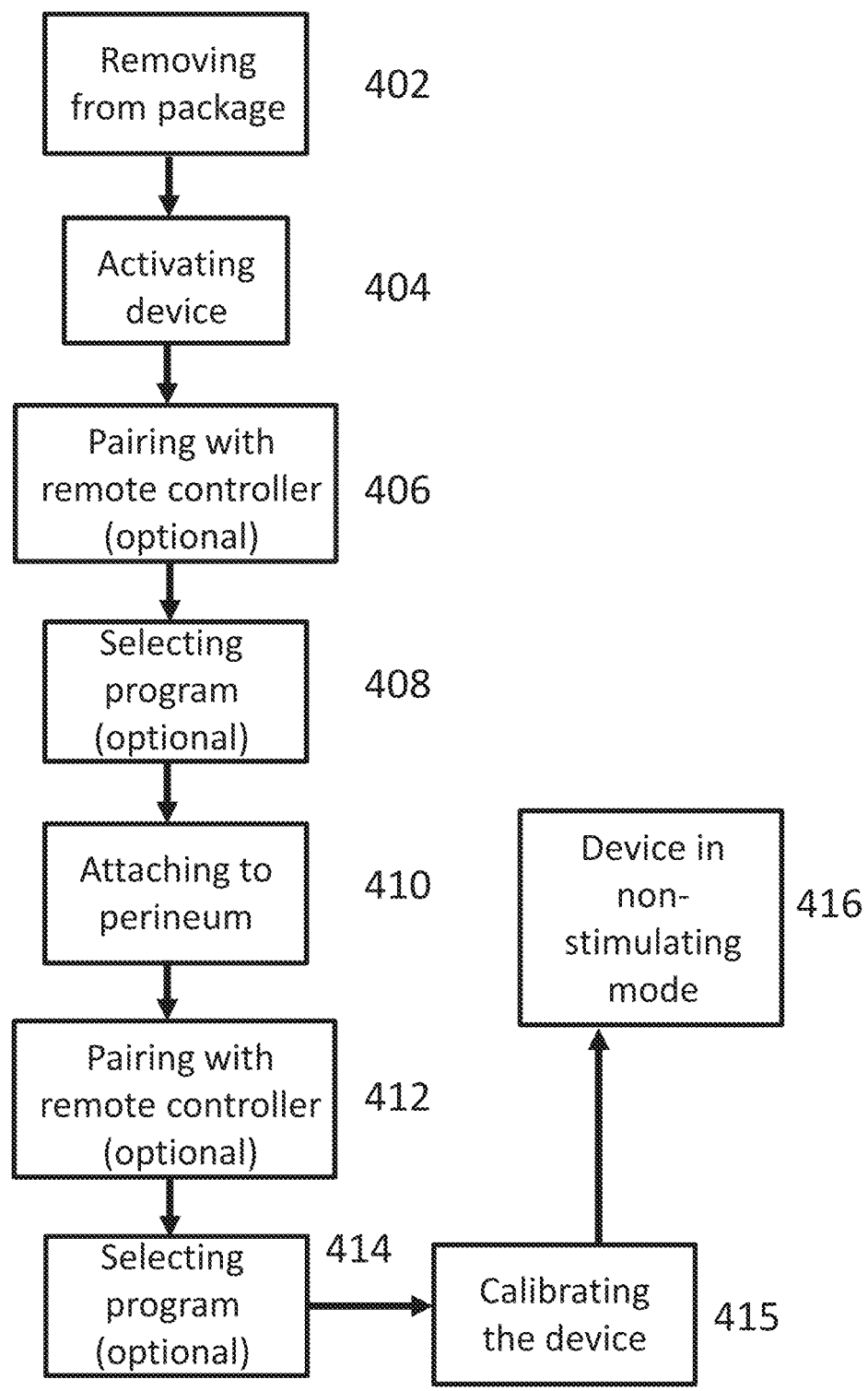
FIG. 4A is a flow chart of a process for activating the device, according to some embodiments of the invention.

According to some exemplary embodiments, the device is configured to be easily applied and activated in order to reduce discomfort and undesired stress of a subject. Reference is now made to FIG. 4A, depicting a process for application and/or initial calibration of the device, according to some exemplary embodiments of the invention.

According to some exemplary embodiments, the device is removed from a package at 402. In some embodiments, the device is a single-use device that is used, for example for several hours, and then it is discarded. Alternatively, the device is removed from the perineum and is stored in the package for further usage.

According to some exemplary embodiments, the device is activated at 404. In some embodiments, the device is activated by pressing an activating button. Alternatively, the device is activated by removing a separating insulator between a battery and electrical conductors. In some embodiments, the device is activated by inserting the battery into the device. In some embodiments, the device is activated while removing the device from the package at 402. Optionally, the device delivers an indication by light and/or sound when the device is activated.

According to some exemplary embodiments, an application program installed on a mobile device, for example a smartphone, a tablet and/or a smartwatch delivers an indication to a user to activate the device. In some embodiments, the mobile device delivers the indication based on an algorithm and/or tables stored in the memory of the mobile device.

According to some exemplary embodiments, the device is paired with a remote controller at 406. In some embodiments, the device is paired with a wearable device and/or a mobile device using Bluetooth wireless signals. Alternatively, the device is paired by WiFi wireless signals with the wearable device and/or the mobile device. In some embodiments, when pairing is complete, the device delivers an indication to the subject. In some embodiments, the indication is delivered by the mobile device and/or the wearable device. In some embodiments, the indication is delivered by sound, light or vibration.

According to some exemplary embodiments, a treatment program or values of at least one electric field parameter are selected at 408. In some embodiments, the selection is made by pressing at least one button on the device. Alternatively or additionally, the selection is made using the application or software program installed on the mobile device or on the wearable device.

According to some exemplary embodiments, the device is attached to the perineum at 410. In some embodiments, the device is attached after the removal of a sticker cover, for example to expose a region covered with glue. In some embodiments, the device is oriented to a desired position using the curves and the cuts, as shown in FIG. 2B.

According to some exemplary embodiments, an application program installed on a mobile device, for example a smartphone, a tablet and/or a smartwatch delivers an indication to a user to attach the device to the perineum. In some embodiments, the mobile device delivers the indication based on an algorithm and/or tables stored in the memory of the mobile device.

According to some exemplary embodiments, the device is paired with a remote controller at 412, after the device is attached to the perineum. In some embodiments, the pairing is performed as described at 412.

According to some exemplary embodiments, a treatment program or values of at least one electric field parameter are selected at 414, after the device is attached to the perineum. In some embodiments, the treatment program or values of at least one electric field parameter are selected as described at 414.

According to some exemplary embodiments, the device is calibrated at 415. In some embodiments, the device is calibrated, for example by intermittently or continuously increasing the electric field intensity until the subject feels uncomfortable and/or pain. The electric field intensity level that causes pain or discomfort is determined as a threshold level. In some embodiments, the electric field intensity is then lowered to a sub-threshold level.

In some embodiments, an automatic calibration process is performed. In some embodiments, in the automatic calibration process, the electric field intensity is increased while monitoring at least one physiological parameter related to the electric field effect. In some embodiments, the electric field intensity is set when a desired effect is reached. In some embodiments, the electric field intensity that was used in prior treatment sessions in the same subject is used.

According to some exemplary embodiments, the device is placed in a non-stimulating mode at 416, for example to save battery power. In some embodiments, the device and/or a mobile device coupled to the device measures and/or calculates at least one physiological parameter. In some embodiments, the at least one physiological parameter is an indicator of the arousal level, excitement level and/or is an ejaculation-indicative parameter. In some embodiments, the at least one physiological parameter comprises the erection level of the penis, blood flow in the penis, heart rate, blood pressure and/or movement of the scrotum or testis.

Figure 4B:
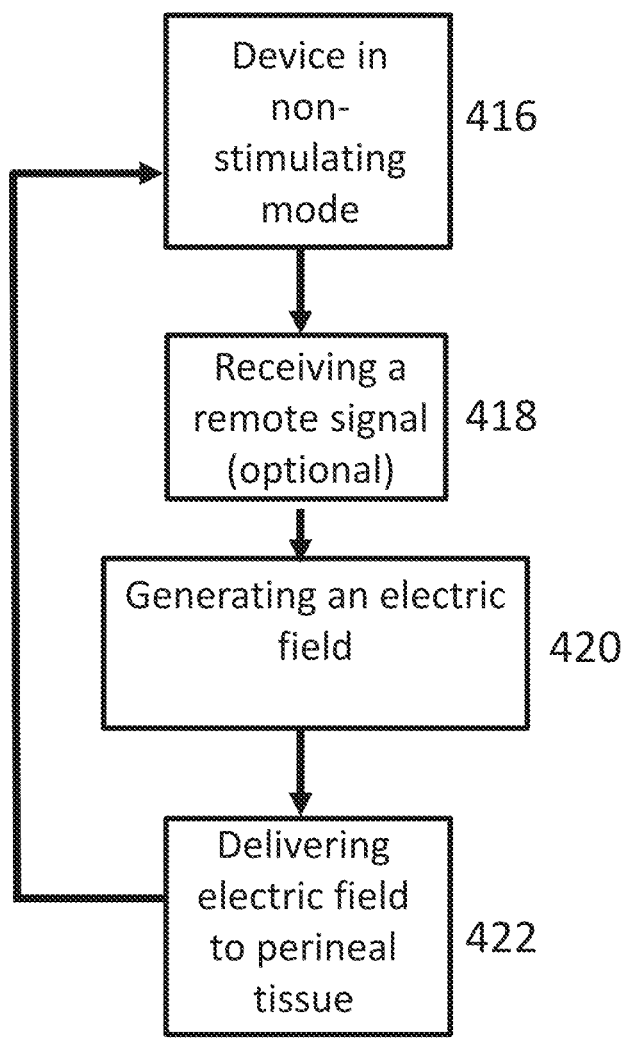
FIG. 4B is a flow chart of a general process for the delivery of an electric field to the perineal tissue, according to some embodiments of the invention.

Reference is now made to FIG. 4B depicting a process for delivery of an electric field to the perineal tissue, according to some exemplary embodiments of the invention.

According to some exemplary embodiments, the device receives a remote signal from a coupled remote device at 418. In some embodiments, the device receives a remote signal from a mobile device and/or the wearable device, optionally using an installed application or program software. In some embodiments, the subject presses a button on the coupled remote device.

According to some exemplary embodiments, an electric field is generated at 420. In some embodiments, the electric field is generated based on the signals received at 418. Alternatively or additionally, the electric field is generated based on a treatment program installed in the memory of the device, for example the memory 220 shown in FIG. 2A or in the memory of the remote controller device, for example a mobile device and/or a wearable device. In some embodiments, the signals received at 418 include values of at least one electric field parameter, used to generate that electric field at 420 based on these values.

According to some exemplary embodiments, the electric field is generated when values of the at least one physiological parameter measured and/or calculated at 416 are larger than predetermined values or are in a range of desired values. In some embodiments, the measured and/or calculated values of the at least one physiological parameter are stored in the memory of the device, for example memory 220 or in a memory of the mobile device. In some embodiments, the predetermined values and/or the range of desired values are stored in the memory of the device, for example memory 220 or in a memory of the mobile device.

According to some exemplary embodiments, the generated electric field is delivered to the perineal tissue at 422. In some embodiments, the electric field is delivered through the electrodes of the device that are placed in contact with the perineal tissue. In some embodiments, the electric field is delivered through selected electrodes of a plurality of electrodes. In some embodiments, the electrodes for the delivery of the electric field are selected based on the desired target type, for example muscles and/or nerves, and the positioned of the desired target inside the perineal tissue, for example the depth of the desired target inside the perineal tissue. In some embodiments, the electric field is delivered for a pre-determined time period, optionally according to the treatment program. In some embodiments, the pre-determined time period is adjusted by a user prior to activation or attachment of the device. Alternatively, the pre-determined time period is adjusted during the activation of the device, for example during the delivery of the electric field. In some embodiments, when the electric field is stopped, the device returns to a non-stimulating mode at 416.

According to some embodiments, the electric field generated at 420 have parameter values selected to allow penetration of the electric field into the perineal tissue to a depth in a range of 2 mm to 30 mm, for example 5 mm, 10 mm, 20 mm, 25 mm or any intermediate, smaller or larger value. In some embodiments, the electric field parameter values are selected to allow penetration of at least 2 mm from the perineum outer surface or the perineum skin and into the perineal tissue.

According to some embodiments, the intensity of the electric field generated at 420 is in a range of 0 mA (milli-amper) to 50 mA, for example 0 mA to 20 mA, 10 mA to 40 mA, 30 mA to 50 mA or any other intermediate range of values. In some embodiments, the intensity of the electric field delivered to the perineal tissue is in a range of 7 mA to 18 mA, for example 7 mA, 10 mA, 12 mA, 15 mA or any intermediate, smaller or larger value.

According to some embodiments, the frequency of the electric field generated at 420 is in a range of 0 Hz (Hertz) to 100 Hz, for example 0 Hz to 50 Hz, 20 Hz to 60 Hz, 50 Hz to 100 Hz or any other intermediate range of values. In some embodiments, the electric field frequency is in a range of 20 Hz-50 Hz, for example 30 Hz, 35 Hz, 40 Hz or any intermediate smaller or larger value.

According to some embodiments, the voltage of the electric field generated at 420 is in a range of 50V (Volt) to 100V, for example 50V, 60V, 70V or any intermediate, smaller or larger value.

According to some embodiments, the interphase interval of the electric field generated at 420 is in a range of 0 μsec to 30 μsec, for example 0 μsec to 10 μsec, 5 μsec to 20 μsec, 15 μsec to 30 μsec or any other intermediate range of values. In some embodiments, the interphase interval is in a range of 10 μsec to 100 μsec, for example 50 μsec, 60 μsec, 70 μsec, 80 μsec, 90 μsec or any intermediate, smaller or larger value.

According to some embodiments, the pulse width of the electric field generated at 420 is in a range of 0 μsec to 800 μsec, for example 0 μsec to 300 μsec, 200 μsec to 600 μsec, 500 μsec to 800 μsec or any other intermediate range of values. In some embodiments, the electric field pulse width is in a range of 250 μsec to 350 μsec, for example 250 μsec, 300 μsec, 350 μsec or any intermediate, smaller or larger value.

According to some embodiments, the ramp time of a stimulation or the electric field delivered at 422 is in a range of 0 μsec to 30 μsec, for example 0 μsec to 15 μsec, 10 μsec to 20 μsec, 15 μsec to 30 μsec or any other intermediate range of values. In some embodiments, the ramp time of the delivered electric field is in a range of 5 μsec to 10 μsec, for example 5 μsec, 7 μsec, 9 μsec or any intermediate, smaller or larger value.

According to some embodiments, the duration of the electric field delivery at 422 is predetermined as continuous or accumulated, for example for safety reasons. In some embodiments, the continuous electric field delivery duration is set to at least 1 minute, for example 7 minutes, 10 minutes, 12 minutes or any intermediate or larger value. Optionally, after reaching the maximal electric field delivery duration, the electric field delivery is stopped. In some embodiments, the accumulated electric field delivery duration is set to at least 1 minute, for example 7 minutes, 10 minutes, 12 minutes or any intermediate value, if the electric field delivery is paused and continued.

Exemplary Modifying Treatment Based on Efficacy

Figure 5A:
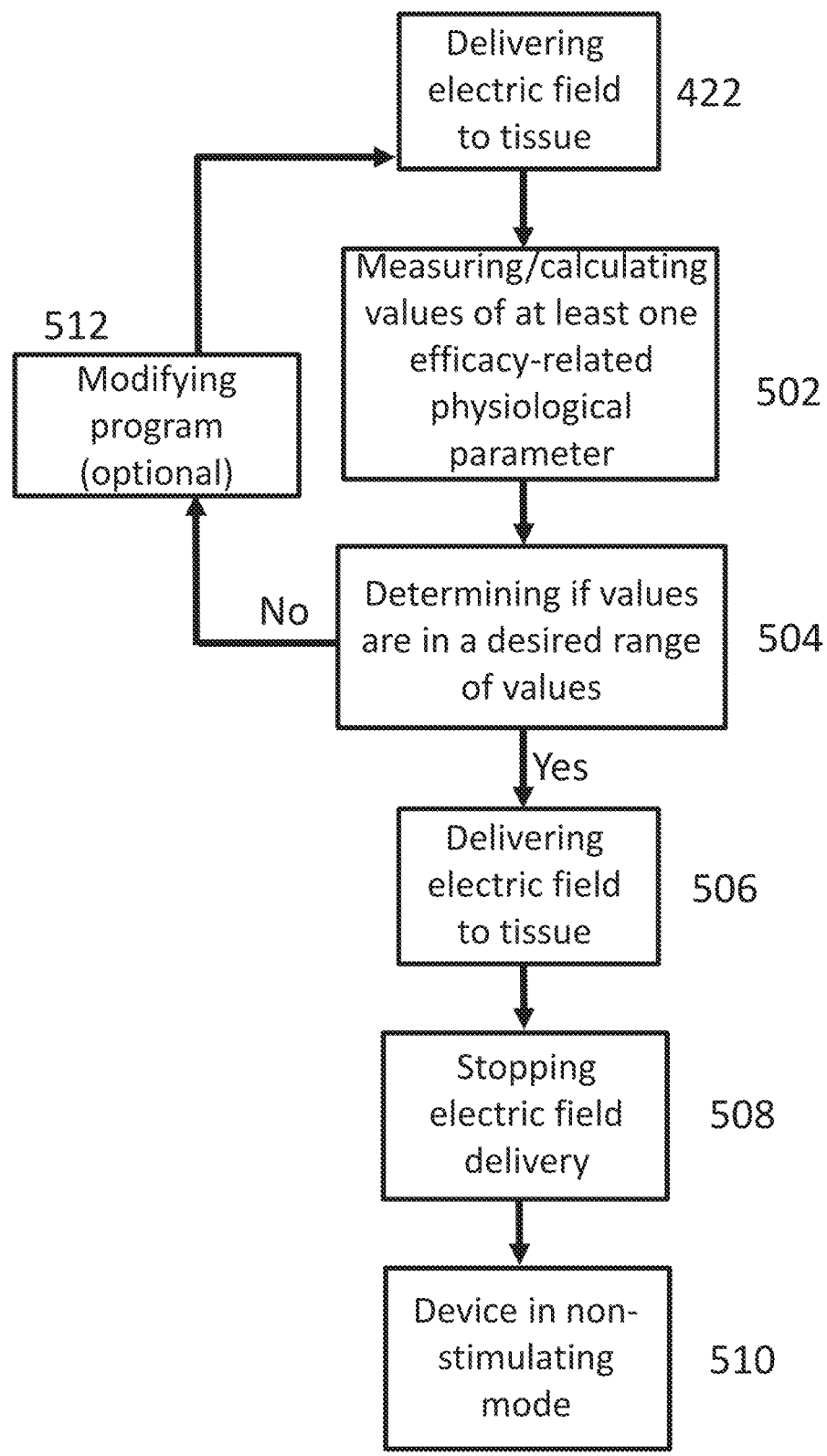
FIGS. 5A and 5B are flow charts of processes for controlling the activation of the device, according to some embodiments of the invention.

Reference is now made to FIG. 5A depicting a process for modifying a treatment program and/or values of at least one electric field parameter based on a measured efficacy parameter, according to some exemplary embodiments of the invention.

According to some exemplary embodiments, the electric field is delivered at 422, or example as previously described at FIG. 4B. In some embodiments, the electric field is generated and delivered according to a treatment program and/or based on electric field parameter values stored in a readable writable memory of the device, for example memory 220.

According to some exemplary embodiments, values of at least one efficacy related physiological parameter are measured and/or calculated at 502. In some embodiments, the values are measured during the application of the electric field. In some embodiments, the efficacy-related physiological parameter comprises electrical activity of muscles and/or nerves at selected regions in the perineal tissue, for example muscles and nerves at regions between the posterior aspect of the scrotum, between the thigh creases skin and in depth of up to 50 mm. Alternatively or additionally, the efficacy-related physiological parameter comprises contraction level of selected muscles in the perineal tissue, for example contraction of the Bulbospongiosus muscle and/or the Ischiocavernosus muscle. In some embodiments, the values are sensed by at least one electrode and/or sensor of the device, for example device 210. In some embodiments, the at least one electrode and/or sensor of the device delivers the sensed values to a control circuitry of the device, for example control circuitry 218. Additionally or optionally, the sensed values are stored in a readable writable memory, for example memory 220 of the device.

According to some embodiments, at least one electrical parameter of the skin, for example impedance is measured, for example by dividing voltage with current at 502. In some embodiments, the electrical parameter of the skin is measured by at least one electrode or at least one sensor of the device which is in an electrical contact with the skin. In some embodiments, the electrical impedance monitoring is used to determine the quality of adhesion of the device to the skin, prior to the delivery of the electric field and/or during the delivery of the electric field. In some embodiments, high impedance values, for example impedance values of at least 5000 ohm, for example 5000 ohm, 6000 ohm, 7000 ohm or any intermediate or larger value indicates that the device has no contact with the skin. In some embodiments, in this case, the device would automatically cease stimulation and optionally signals a mobile device, for example a smartphone to deliver an alert to the user.

According to some exemplary embodiments, low impedance values, for example impedance values of 1000 ohm and lower, for example 900 ohm, 800 ohm, 700 ohm or any intermediate or smaller value would indicate that the device is properly contacting the skin. In some embodiments, in this case, the device would signal the smartphone to deliver an indication to the user that the device is properly attached to the skin.

According to some exemplary embodiments, measured impedance values in a range between 1000 ohm and 5000 ohm indicates that the device is sub-optimally applied to the skin. In some embodiments, in this case, the device would signal the smartphone to generate a warning indication to the user. In some embodiments, a gradual decrease in impedance values, for example at a rate of at least 50 ohm per second, for example 50 ohm per second, 100 ohm per second, 500 ohm per second or any intermediate lower or higher decrease rate is an indicator of nerve activity which may indicate of approaching ejaculation and/or urination.

According to some exemplary embodiments, the device determines if the measured values of the efficacy related physiological parameter are in a desired range of values, at 504. In some embodiments, the control circuitry of the device determines if the measured values are in a desired range of values by comparing the measured values to at least one table or to pre-determined values stored in the memory. Alternatively or additionally, the control circuitry of the device determines if the measured values are in a desired range of values using at least one algorithm and/or software program stored in the memory of the device. In some embodiments, the control circuitry of the device determines if the measured values are in a desired range of values by transmitting the measured values to a cloud, for example cloud 310, and optionally using at least one table, algorithm and/or a software program stored in the cloud. Alternatively, the control circuitry of the device determines if the measured values are in a desired range of values by transmitting the measured values to an external device, for example mobile device 308 or wearable device 306 and optionally using at least one table, algorithm and/or a software program stored in the external device.

According to some exemplary embodiments, if the measured values are not in a desired range of values, then the treatment program or at least one parameter of the treatment program is modified at 512, optionally automatically, by the device. In some embodiments, if the measured values are not in a desired range of values then a different treatment program is selected, optionally by the control circuitry, from a plurality of treatment programs stored in the memory of the device. Alternatively or additionally, at least one parameter of the electric field is modified, for example the frequency and/or the intensity of the electric field. Optionally, the control circuitry of the device increases or decreases the frequency and/or the intensity levels of the electric field. In some embodiments, the treatment program and/or the at least one electric field parameter are modified while delivering the electric field to the tissue. Alternatively, the electric field delivery is stopped and continues after the treatment program and/or the at least one electric field parameter are modified.

According to some exemplary embodiments, if the measured values are in a desired range of values than the electric field is delivered to the perineal tissue at 506, according to the treatment program or based on the electric field parameter values used at 422.

According to some exemplary embodiments, the electric field delivery is stopped at 508. In some embodiments, the electric field delivery is stopped according to the treatment program. Alternatively, the electric field delivery is stopped when a signal is received from a user of the device, for example using the mobile device or a wearable device wirelessly connected to the device. In some embodiments, the electric field delivery is stopped based on measured physiological signals, for example when the device detects physiological signals related to the desire of a user to ejaculate. Optionally, the electric field delivery is stopped when the device, the mobile device and/or wearable device receives a voice command for stopping the delivery of the electric field.

According to some exemplary embodiments, when the electric field is stopped, the device moves to a non-stimulating mode at 510. In some embodiments, in a non-stimulating mode the device waits to receive an activating wireless signal to resume the generation and the delivery of the electric field. Optionally, if an activating wireless signal is received, the device delivers an electric field to the tissue based on the last program and/or last electric field parameter values used, that are stored in the readable writable memory of the device. In some embodiments, the device is a single-use device, therefore the last program and/or last electric field parameter values are stored on the mobile device, for example in the application program installed on the mobile device.

Exemplary Modifying Treatment Based on Safety

Figure 5B:
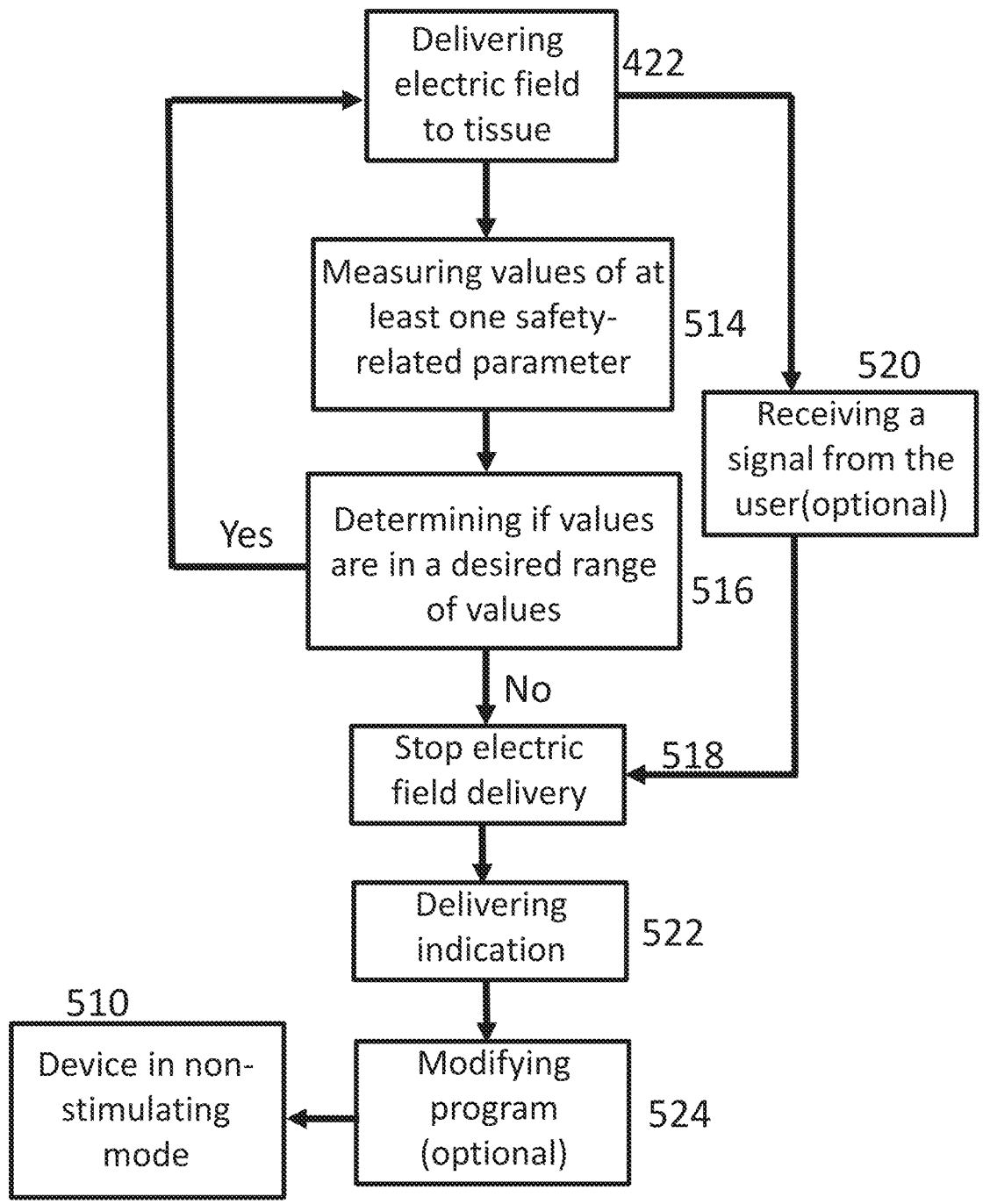

Reference is now made to FIG. 5B depicting a process for delivery of an electric field while monitoring safety related parameters, according to some exemplary embodiments of the invention.

According to some exemplary embodiments, the electric field is delivered at 422, or example as previously described in FIG. 4B and FIG. 5A. In some embodiments, the electric field is generated and delivered according to a treatment program and/or based on electric field parameter values stored in a readable writable memory of the device, for example memory 220.

According to some exemplary embodiments, values of at least one safety related parameter, for example a physiological parameter is measured and/or calculated at 514. In some embodiments, the values are measured during the application of the electric field. In some embodiments, the safety-related physiological parameter comprises electrical activity of muscles and/or nerves at selected regions in the perineal tissue, for example regions proximal to posterior aspect of the scrotum, and/or regions proximal to the anus, and/or regions proximal to each of the creases of the thighs. Alternatively or additionally, the safety-related physiological parameter comprises contraction level of selected muscles in the perineal tissue, for example the bulbospongiosus muscle and/or the, ischiocavernosus.

In some embodiments, the values are sensed by at least one electrode and/or sensor of the device, for example device 210. In some embodiments, the at least one electrode and/or sensor of the device delivers the sensed values to a control circuitry of the device, for example control circuitry 218. Additionally or optionally, the sensed values are stored in a readable writable memory, for example memory 220 of the device.

According to some exemplary embodiments, the device measures at least one electrical parameter of the skin, for example impedance during application of the electric field and/or electrical parameters related to the generate electric field. In some embodiments, removing the device from the skin during electric field delivery causes an increase, optionally a rapid increase in current and/or power density and/or impedance. In some embodiments, the device stops the electric field delivery if such an increase is detected.

According to some exemplary embodiments, the device determines if the measured values of the safety related parameter are in a desired range of values, at 516. In some embodiments, the control circuitry of the device determines if the measured values are in a desired range of values by comparing the measured values to at least one table or to pre-determined values stored in the memory. Alternatively or additionally, the control circuitry of the device determines if the measured values are in a desired range of values using at least one algorithm and/or software program stored in the memory of the device. In some embodiments, the control circuitry of the device determines if the measured values are in a desired range of values by transmitting the measured values to a cloud, for example cloud 310, and optionally using at least one table, algorithm and/or a software program stored in the cloud.

Alternatively, the control circuitry of the device determines if the measured values are in a desired range of values by transmitting the measured values to an external device, for example mobile device 308 or wearable device 306 and optionally using at least one table, algorithm and/or a software program stored in the external device.

According to some exemplary embodiments, if the measured values are not in a desired range of values or are higher or lower compared to a predetermined safety threshold, then the electric field delivery is sopped at 518, optionally automatically, by the device.

According to some exemplary embodiments, if the measured values are in a desired range of values or lower or higher from a predetermined safety threshold then the electric field is delivered to the perineal tissue at 506, according to the treatment program or based on the electric field parameter values used at 422.

According to some exemplary embodiments, a signal is received from a user at 520. In some embodiments, the signal is received from the user during the delivery of the electric field to the perineal tissue of the user. Alternatively, a signal is received from a user between the delivery of electric field pulses or after the delivery of the electric field. In some embodiments, the signal is received from an external device, for example a mobile device and/or a wearable device. In some embodiments, the user delivers the signal in response to a pain sensation at the perineal tissue or in other parts of the body. Alternatively or additionally, the user delivers the signal in response to discomfort sensation.

According to some exemplary embodiments, when a signal related to pain or discomfort is received by the device, the electric field delivery is stopped at 518. Alternatively, at least one parameter of the electric field is modified, for example the intensity of the electric field is lowered.

According to some exemplary embodiments, an indication is delivered by the device to the user at 522, for example when the electric field delivery is stopped. In some embodiments, the indication comprises a sound indication and/or a vibration indication. Alternatively, the device signals an external device, for example a mobile device or a wearable device to generate the indication. In some embodiments, the indication generated by the external device comprises a sound indication and/or a light indication. Optionally all indications by the device or by the external devices are human detectable indications.

According to some exemplary embodiments, at least one treatment program parameter is modified at 524. In some embodiments, at least one parameter of the delivered electric field is modified, for example lowering the intensity of the electric field and/or modifying the frequency of the delivered electric field. Alternatively or additionally, the delivery duration of the electric field is modified, for example shortening the delivery duration of the electric field to the perineal tissue.

According to some exemplary embodiments, the device moves to a non-stimulating mode at 510. In some embodiments, in a non-stimulating mode the device waits to receive a signal from a user in order to generate and/or to deliver an electric field to the user.

Exemplary Activation of the Device by a User

Figure 5C:
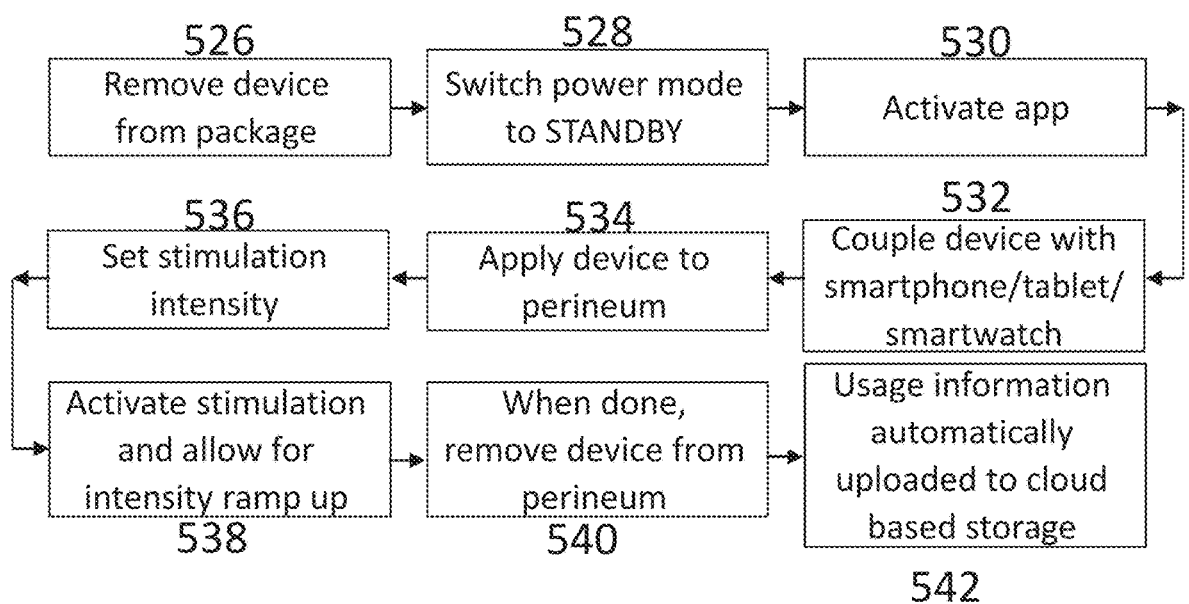
FIG. 5C is a flow chart of a process for using the device, according to some exemplary embodiments.

According to some exemplary embodiments, the device is designed to be applied by a user to the perineum before sexual intercourse. In some embodiments, the device is removed from the perineum and discarded after the sexual intercourse or can be re-used by the user. Reference is now made to FIG. 5C depicting a process of using the device by a user, according to some exemplary embodiments of the invention.

According to some exemplary embodiments, a user removes the devise from a package at 526. In some embodiments, when unpacking the device, the user tears the package along marked lines, for example not to damage the device. Alternatively or additionally, the user tears the package at specific marked location which are distant from the packed device.

According to some exemplary embodiments, the user switches a power mode of the device to a standby mode, at 528. In some embodiments, the power mode is switched by a switch or a selection button positioned on the housing of device, for example housing 212 shown in FIG. 2A. Optionally the switch or the selection button is part of the interface 226 of the device. In some embodiments, removal of an isolator between at least one battery, for example battery 222, shifts the power mode to a stand-by mode. In some embodiments, the power switch or button switches the power mode between OFF, Standby and ON. Optionally, the power switch or button is mechanical, magnetic or an isolation tab which exposes contacts and close circuit when removed.

According to some exemplary embodiments, a software application (app) installed in a mobile device, for example a smartphone is activated at 530. In some embodiments, a user couples the device with a smartphone at 532. Alternatively or additionally, the device is coupled with a tablet or a smartwatch. In some embodiments, the device is coupled with smartphone only after an identification process is completed. In some embodiments, to prevent unauthorized coupling, an identification process, which optionally comprises insertion of a password to allow coupling, is performed.

According to some exemplary embodiments, the device is applied to the perineum at 534. In some embodiments, the device is applied to the perineum by exposing at least one adhesive tape located on the device housing, and attaching the at least one adhesive tape to the perineum skin. In some embodiments, the device is oriented during application according to markings or geometrical shapes or geometrical cuts or curves in the device housing. In some embodiments, the device is bent along axial bending lines in the device housing to conform to the anatomical curves of the perineum, for example to conform to the anatomical curve of the perineum between the two legs, for example as shown in FIG. 2C. Alternatively or additionally, the device is bent along axial bending lines in the device housing to conform to the anatomical curve of the perineum between the scrotum and the anus.

According to some exemplary embodiments, the stimulation parameters, for example stimulation intensity are set at 536. In some embodiments, the stimulation parameters set using the software program installed in the mobile device coupled to the device, for example the smartphone and/or tablet and/or smartwatch. In some embodiments, the stimulation parameters are set based on the parameters values stored in the memory of the mobile device. In some embodiments, a device calibration is performed by increasing the stimulation intensity until a user senses discomfort and/or pain, and then reducing the intensity level in at least 0.1 mA, for example 0.1 mA, 0.2 mA, 0.3 mA, 0.5 mA or any intermediate or larger reduction value, to reach for example a subthreshold intensity level. Alternatively, the stimulation intensity is set to previously used intensity levels.

According to some exemplary embodiments, stimulation is activated at 538. In some embodiments, stimulation is activated by delivering the electric field to selected targets in the perineal tissue. In some embodiments, the intensity increases after stimulation is activated to a pre-determined level, for example the intensity level set at 536. In some embodiments, when the stimulation is activated, for example when the electric field is delivered to perineal tissue, selected muscles are affected and delay ejaculation, for example the Bulbospongiosus muscle and/or the Ischiocavernosus muscle.

According to some exemplary embodiments, after ejaculation or after the sexual intercourse, the device is removed from the perineum at 540. In some embodiments, the device is discarded. Alternatively, the device is stored for an additional use.

According to some exemplary embodiments, usage information and/or log files are uploaded, optionally automatically, to a cloud based storage, for example cloud 310 shown in FIG. 3, at 542. Alternatively or additionally, the usage information and/or log files are stored in the writable readable memory, for example memory 220 shown in FIG. 2A of the device. In some embodiments, the usage information and/or log files are stored in a memory of an external device, for example mobile device 308 and/or wearable device 306 shown in FIG. 3.

Exemplary Monitoring an Ejaculation-Indicative Parameter

According to some exemplary embodiments and without being bound to any theory, premature ejaculation is characterized by ejaculation which always or nearly always occurs prior to or within about one minute of vaginal penetration. In some embodiments, application of an electric field for example, for stimulation of selected targets in the perineal tissue delays ejaculation in at least 10 seconds, for example 10 seconds, 15 seconds, 30 seconds, 1 minute, 5 minutes, 10 minutes or any intermediate or larger value. Optionally, application of an electric field delays ejaculation in at least 2 fold from the base line duration until ejaculation, for example 2 fold, 3 fold, 3.5 fold or any intermediate smaller or larger value. In some embodiments, a device for delivery of the electric field measures values of at least one ejaculation indicative parameter and optionally sets the timing for delivery of the electric field to the desired tissue. In some embodiments, a gradual decrease in impedance values, for example at a rate of at least 50 ohm per second, for example 50 ohm per second, 100 ohm per second, 500 ohm per second or any intermediate lower or higher decrease rate is an indicator of nerve activity which may indicate of approaching ejaculation and/or urination.

Figure 6A:
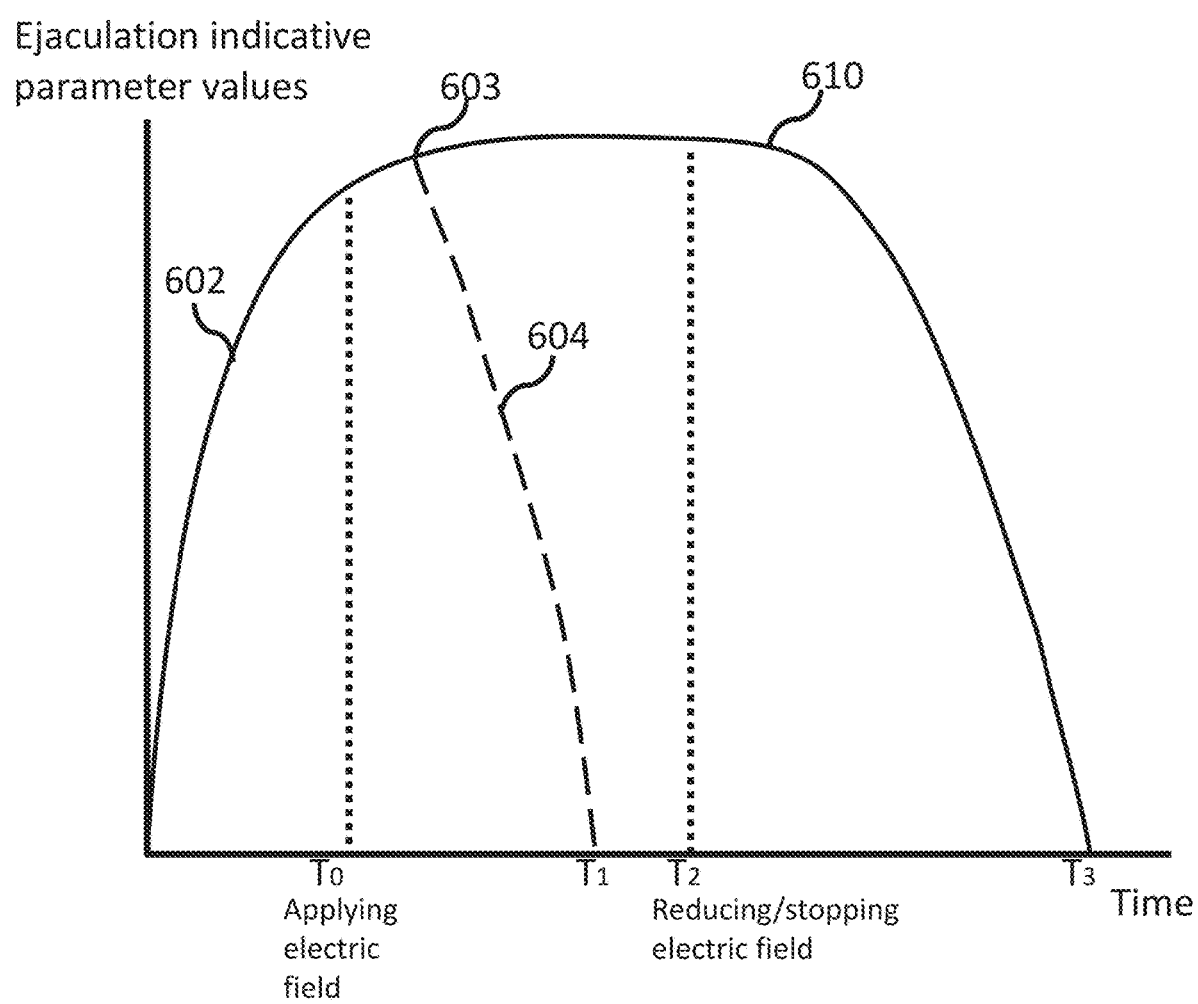
FIG. 6A is a graph of the stimulation effect on delaying ejaculation, according to some embodiments of the invention.

Reference is now made to FIG. 6A depicting changes in time of values of an ejaculation indicative parameter under premature ejaculation conditions and in response to application of an electric field as described in this application, according to some exemplary embodiments of the invention.

According to some exemplary embodiments, values of at least one ejaculation parameter are increased at 602. In some embodiments, when an electric field is not applied to the perineal tissue, ejaculation occurs at 604 and ends at T1. In some embodiments, in order to delay ejaculation, an electric field is applied at TO. In some embodiments, the electric field is applied prior to reaching the point of controlled ejaculation initiation 603. In some embodiments, the applied electric field delays ejaculation until point 610 and therefore ejaculation ends at T3. Optionally, the device reduces or stops the electric field at T2 to initiate controlled ejaculation at point 610.

According to some exemplary embodiments, the applied electric field temporarily inhibits the rhythmic contractions of the bulbospongiosus muscle. In some embodiments, the ejaculation indicative parameter comprises the contraction level of the Bulbospongiosus muscle or a gradual decrease in impedance values, as described above. In some embodiments, the device measures the ejaculation indicative parameter values by at least one electrode or sensor in the device. In some embodiments, the control circuitry of the device, for example control circuitry 218 shown in FIG. 2A, signals to generate and to deliver the electric field based on the measured values. Optionally, the control circuitry determined the timing for application of the electric field and/or at least one parameter of the electric field, for example the intensity, based on the measured values.

Figure 6B:
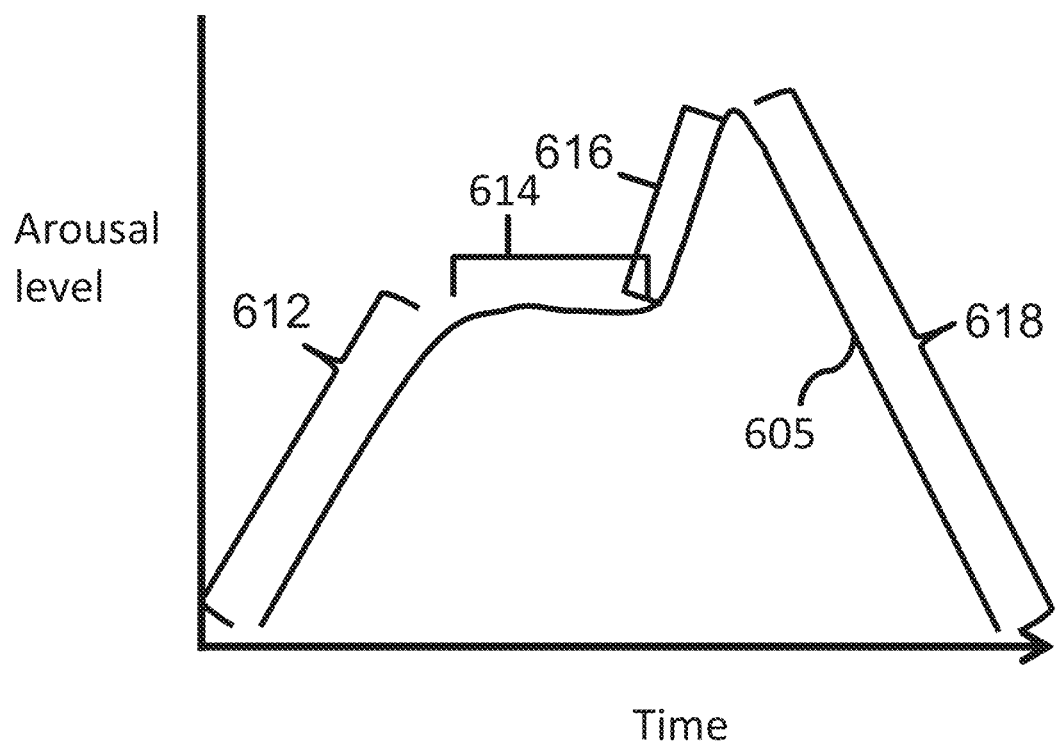
FIGS. 6B and 6C are graphs of a sexual response cycle in healthy subjects, in subjects suffering from premature ejaculation and in subjects suffering from premature ejaculation after delivery of an electric field, according to some embodiments of the invention.
Figure 6C:
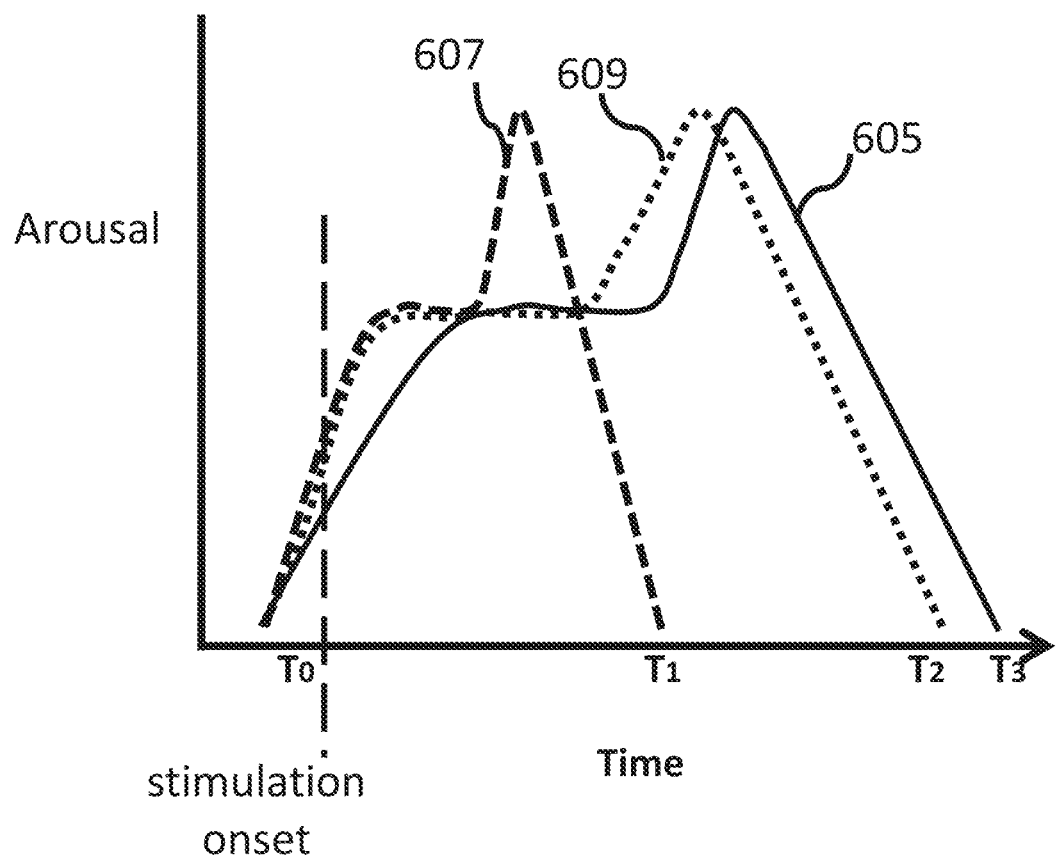
Figure 6D:
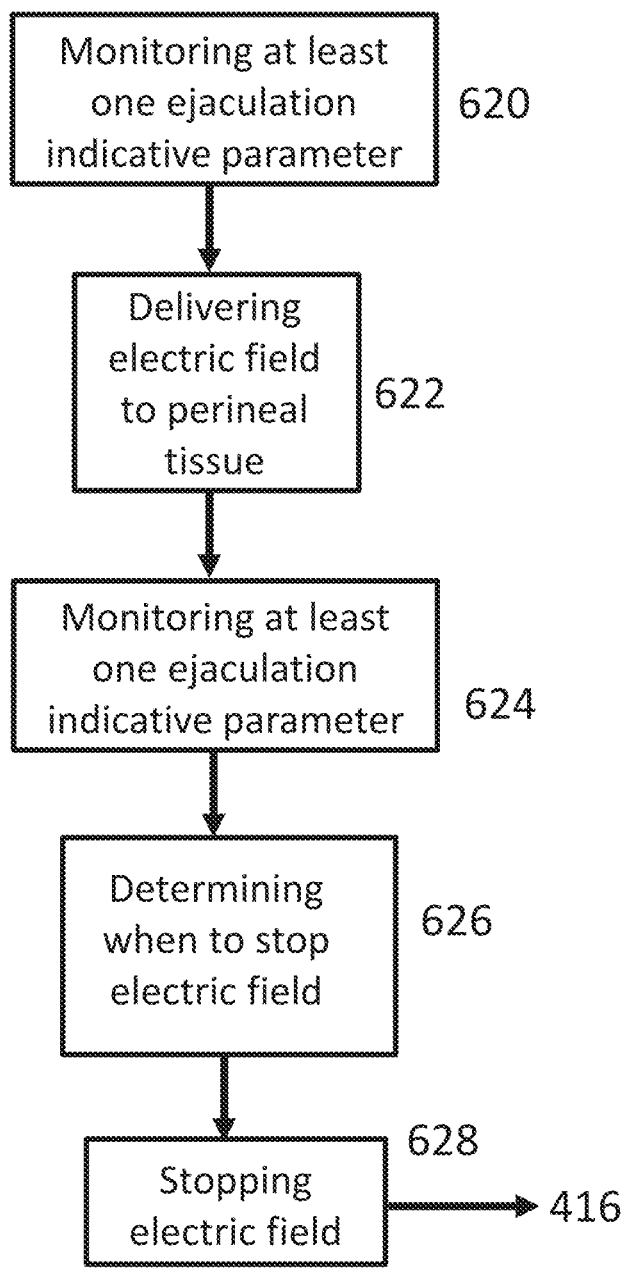
FIG. 6D is a flow chart of a process for controlling the delivery of an electric field based on measurements of an ejaculation-indicative parameter, according to some embodiments of the invention.

Reference is now made to FIGS. 6B and 6D depicting changes in arousal levels in healthy subjects, subjects suffering from premature ejaculation and in response to electric field application by the device, according to some exemplary embodiments of the invention.

According to some exemplary embodiments and without being bound by any theory, the sexual response cycle in humans is divided into 4 main phases, an excitement phase 612, a plateau phase 614, an orgasm phase 616 and a resolution phase 618, for example as shown in FIG. 6B and as described, for example, in Donnatuci C F. Etiology of ejaculation and pathophysiology of premature ejaculation. J Sex Med, 2006. In subjects suffering from premature ejaculation (PE), for example as shown in FIG. 6C graph 607, the plateau phase is shorter compared to the plateau phase in healthy subjects shown in graph 605. Additionally or optionally, the excitement phase is also shorter in PE subjects compared to the excitement phase in healthy subjects. According to some exemplary embodiments, application of an electric field in PE subjects during the excitement phase, for example as shown in FIG. 6C graph 609, prolongs the plateau phase in at least 10 seconds, for example 10 seconds, 30 seconds, 60 seconds, 5 minutes, 10 minutes or any intermediate smaller or larger value.

According to some exemplary embodiments, the device delivers an electric field in response to signals received from a mobile device, for example a smartphone, tablet or smartwatch. In some embodiments, the electric field is delivered and/or stopped in response to a voice command delivered by a user of the device. In some embodiments, the voice command is received by the device and/or by the mobile device.

According to some exemplary embodiments, the electric field onset is determined based on the duration of the excitement phase in each PE subject. In some embodiments, the electric field onset is determined by a user of the device or an expert, for example a physician or a surrogate. In some embodiments, the expert determines the electric field parameters, for example stimulation intensity, stimulation duration and/or stimulation onset. In some embodiments, the device measures at least one physiological parameter during the sexual response cycle in a subject, for example during the excitement phase, during the plateau phase and/or during the orgasm phase to determine the stimulation (electric field) onset, stimulation duration, stimulation intensity or any other parameter related to the stimulation or the treatment delivered by the device.

According to some exemplary embodiments, the electric field is delivered prior to the excitement phase. Alternatively, the electric field is delivered automatically by the device during the excitement phase, for example when values of at least one physiological parameter are higher than a pre-determined value or are in a range of desired values. In some embodiments, the at least one physiological parameter is measured by the device and/or by at least one sensor connected to the device or to the mobile device. Alternatively or additionally, the at least one physiological parameter is measured by the mobile device.

Reference is now made to FIG. 6D depicting a process for applying, optionally automatically, an electric field to the inhibit ejaculation based on measurements of an ejaculation-indicative parameter, according to some exemplary embodiments of the invention. In some embodiments, the process is optionally a fully automatic process, where, for example the device determines when to deliver and when to stop delivering the electric field based on ejaculation-indicative physiological parameters measured by at least one electrode and/or at least one sensor of the device.

According to some exemplary embodiments, the device monitors values of at least one ejaculation indicative parameter at 620. In some embodiments, the values of the ejaculation indicative parameter are sensed by at least one electrode or at least one sensor of the device, placed in contact with the perineum. In some embodiments, the device monitors at least one physiological parameter prior to and/or during the excitement phase, for example excitement phase 612. In some embodiments, the at least one physiological parameter indicates the progression of the excitement phase. In some embodiments, the at least one physiological parameters comprises arousal level, erection level, blood flow inside the penis, movement of the scrotum or testis.

According to some exemplary embodiments, the device delivers an electric field to selected targets in the perineal tissue at 622. In some embodiments, the device initiates the delivery of the electric field when values of the at least one ejaculation indicative parameter reach a pre-determined level, stored for example in the readable writable memory, for example memory 220 of the device. In some embodiments, the device delivers an electric field to the perineal tissue if values of the at least one physiological parameter measured prior to and/or during the excitement phase are higher than a pre-determined value or are in a desired range of values. In some embodiments, the measured values and/or the pre-determined values and/or the desired range of values are stored in the readable writable memory of the device or in the memory of the mobile device coupled to the device.

According to some exemplary embodiments, the ejaculation-indicative parameter is monitored while the electric field is delivered at 624. In some embodiments, the control circuitry of the device measures the values of the parameter and determines when to stop the delivery of the electric field at 626 based on said measured values and using at least one algorithm, at least one table and/or at least one software program in memory 220. Optionally, the control circuitry compares the measured values to values stored in the memory 220. In some embodiments, the ejaculation-indicative parameter and/or the at least one physiological parameter and/or other one or more physiological parameters are measured during the plateau phase 614 and/or during the orgasm phase 616 and optionally during the resolution phase 618. In some embodiments, the ejaculation-indicative parameter and/or the at least one physiological parameter are measured during the entire sexual response cycle, for example the sexual response cycle described in FIG. 6B.

According to some exemplary embodiments, the device stops the electric field at 628, based on the determining results at 626. In some embodiments, when the electric field delivery stops, the device is placed in a non-stimulating mode at 416.

According to some exemplary embodiments, the device is set to a learning mode, where an electric field is not applied. In some embodiments, when the device is in a learning mode, the device measures at least one ejaculation indicative parameter or any other physiological parameter that allows to determine when to deliver an electric field and optionally when to stop the delivery of the electric field. In some embodiments, based on the measured parameter, the device generates a personalized treatment plan, which includes timing and/or electric field parameter values that are adjusted to a specific user. In some embodiments, the personalized treatment plan is generated by a software application installed in the mobile device, for example mobile device 308 and/or by at least one algorithm and/or software program installed in the cloud, for example cloud 310.

Exemplary Application Software

According to some exemplary embodiments, the device is controlled by an app installed in a mobile device, for example a smartphone. In some embodiments, the app delivers indications and alerts to a user of the device, for example by sound, by light or by vibration. In some embodiments the app deliver indications, for example visual indications related to the battery of the device, the activation state of the device, the electric field parameter values or any other parameter related to the device or the treatment program.

In some embodiments, the app serves to control the parameters of the delivered electric field and/or the parameters of the treatment, for example by selecting values of the parameters. Additionally, the app allows to initiate and/or to terminate the delivery of an electric field, optionally by a user or any other subject.

According to some exemplary embodiments, the app presents historical usage information of a single user, as well as comparative information of multiple users, optionally anonymous users. In some embodiments, the app enables the user to upload his usage information, for example date and time of use, stimulation intensity, duration of use and/or electrical impedance to a cloud based storage, for example cloud 310. In some embodiments, each individual device is identified using a Device ID—a visible alphanumeric series for device identification and, Encrypted ID—alphanumeric series for device identification while transferring usage information. In some embodiments, in this way, the identity and privacy of the user are maintained. In some embodiments, the app stores in a memory the intensity value of the last stimulation session or an average stimulation intensity value, and allow the user easier and quicker stimulation activation. In some embodiments, when the device comprises an array of electrodes, the app stores the combination of electrodes used for the last stimulation.

According to some exemplary embodiments, launching the app and/or when the device is in a non-stimulating mode and/or when the device delivers the electric field, activates the smartphone's Kiosk Mode, meaning only emergency functions are operational and all other functions are temporarily disabled for the duration of stimulation. In some embodiments, this feature is used for safety reasons and/or to help the user avoid distractions during sexual intercourse.

According to some exemplary embodiments, in case the smartphone's battery is not charged enough, the app may render the activation of the device disabled. In some embodiments this feature can be preprogrammed into the processor and be preset to 5% or 10% or 20% of the current capacity/charge status of the battery of the smartphone. In some embodiments, the device automatically pauses stimulation in case connectivity between device and smartphone/app is lost. Alternatively, when the connection between the smartphone and the device is lost, the device continues to deliver the electric field based on a program and/or on electric field parameter values stored in the memory of the device. Optionally, when setting the electric field parameters or any treatment parameter by the app, the settings are wirelessly transmitted to the device and are stored in the memory, for example memory 220 of the device. In some embodiments, storing the settings in the memory 220 allows, for example to deliver the electric field to the perineal tissue when the connection between the device and the smartphone is lost.

According to some exemplary embodiments, when the app is coupled to the device, the software program and/or algorithms and/or tables stored in the memory 220 of the device are updated.

According to some exemplary embodiments, the application program, for example the app, delivers usage instructions stored in the memory of the mobile device and/or in a cloud storage, to the user.

According to some exemplary embodiments, the application program recommends a treatment protocol and/or electric field parameter values and/or modifies a treatment protocol based on data received from the user and/or from an expert, for example clinical data of the user, list of diseases, list of medications taken by the user, and/or estimated time to sexual intercourse.

In some embodiments, the clinical data comprises weight, body-mass index (BMI), age and/or clinical history of the subject. In some embodiments, the treatment protocol comprises the activation time of the device, attachment time of the device and/or other parameters related to the electric field delivery.

In some embodiments, the application program recommends a treatment protocol and/or electric field parameter values and/or modifies a treatment protocol using at least one table or at least one algorithm included in the application program or in a memory of the mobile device, for example in the memory of the smartphone, tablet and/or smartwatch. In some embodiments, the application program suggests a modified treatment protocol with optionally modified electric field parameter values if a subject is treated for ED, for example by Viagra®, Stendra, Cialis, Levitra and/or Staxyn. In some embodiments, the application program determines which treatment protocol to select and/or which electric field parameter values to select using at least one table and/or at least one algorithm stored in the memory of the mobile device, for example smartphone, tablet and/or smartwatch.

Exemplary Operation with Other Products

According to some exemplary embodiments, data provided by manufactures of other products can allow a user of the device to access premium features in the application program. In some embodiments, manufacturers can place an access code/barcode/QR code on the packaging of their relevant products, for example condoms, erectile dysfunction drugs, lubricants, etc. In some embodiments, these codes are identified by the app controlling the device and offer the user of the patch premium features, for example additional features that are not included in his program application. In some embodiments, for example, a user who purchases both Viagra pills and the device, can use access codes or any data on the package of the pills to access premium features in the application program, for example his personal usage history of the devices.

In some embodiments, premium features the device are application program/software based and comprise personal usage history, for example number of uses, duration of use, improvement rate, on-line ordering of patches, on-line prescription delivery. Optionally, the premium features are software/hardware embedded features, for example extending the delivery duration of the electric field relative to an existing treatment protocol, for example from 5 minutes to 7 minutes or to 10 minute.

It is expected that during the life of a patent maturing from this application many relevant devices for delivery of an electric field will be developed; the scope of the terms stimulation or electric field is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A device for electrifying perineal tissue, comprising:
a housing shaped and sized to be positioned on a perineum surface of a subject between a posterior aspect of a scrotum and an anus of said subject, wherein said housing comprises an attachment element configured to attach a surface of said housing to said perineum surface of said subject and to keep said device attached to said perineum surface between said posterior aspect of the scrotum and said anus during sexual intercourse;
at least two electrifying electrodes in said housing, positioned entirely on a skin surface between said posterior aspect of the scrotum and the anus, said at least two electrifying electrodes configured to deliver an electric field to a bulbospongiosus muscle of said subject and/or innervating nerves thereto;
a control circuitry in said housing;
a pulse generator in said housing electrically connected to said at least two electrifying electrodes and said control circuitry,
wherein said control circuitry is configured to signal said pulse generator to generate the electric field in accordance with at least one electric field parameter comprising a pre-determined electric field intensity level and at least one treatment parameter comprising a ramp time of at least 5 seconds, whereby said generated electric field increases to reach said pre-determined intensity level during said ramp time; and
said at least one electric field parameter, including said intensity level, and said at least one treatment parameter, including said ramp time, are selected to inhibit rhythmic contractions of said bulbospongiosus muscle and affect a physiological ejaculatory process in said subject during said delivery of said electric field when said device is attached to said perineum surface during said sexual intercourse.

2. A device according to claim 1, wherein a distance between the at least two electrifying electrodes is between 10 to 14 mm.

3. A device according to claim 1, wherein said housing is thin and flexible enough to bend and conform to the anatomical curvature of the perineum.

4. A device according to claim 1, wherein said pulse generator is configured to generate and deliver an electric field configured to prolong an Ejaculatory Latency Time (ELT) in at least two-fold compared to the ELT duration without electric field delivery.

5. A device according to claim 1, comprising at least one sensor in said flexible housing for measuring at least one physiological parameter.

6. A device according to claim 1, wherein said device is connected to at least one sensor configured to measure at least one physiological parameter.

7. A device according to claim 5, wherein said at least one physiological parameter comprises heart rate.

8. A device according to claim 1, wherein said device comprises at least one electrode or sensor for measuring impedance of the generated electric field, and wherein said device is further configured to perform at least one of:
generating a human detectable indication when values of said measured impedance are higher than 3000 ohm; and
stop generating said electric field if said measured impedance values are higher than 5000 ohm.

9. A device according to claim 1, wherein said device comprises at least one electrode or sensor for measuring values of at least one electrical parameter of the electric field, and wherein said control circuitry calculates impedance based on said measured values of said at least one electrical parameter of the electric field.

10. A device according to claim 1, wherein said housing comprises at least one longitudinal bending line for bending the device to conform to the anatomical curvature of the perineum between the creases of the thighs.

11. A device according claim 1, wherein said housing comprises at least one transverse bending line for bending the device to conform to the anatomical curvature of the perineum between the posterior aspect of the scrotum and the anus.

12. A device according to claim 1, wherein said housing comprises a proximal region with an inward curve shaped and sized to generally follow a posterior aspect of the scrotum and a distal region shaped and sized to be positioned near the anus.

13. A device according to claim 1, wherein a surface area of said at least two electrifying electrodes is in a range between 90 mm² and 850 mm².

14. A device according to claim 1, comprising at least one sensor or electrode electrically connected to said control circuitry for measuring values of at least one physiological parameter of said subject, and wherein said control circuitry is further configured to signal said pulse generator to generate said electric field if said measured values are higher than a predetermined value and/or if said measured values are in a desired range.

15. A device according claim 1, wherein said at least one selected target comprises the bulbospongiosus muscle, nerves innervating the bulbospongiosus muscle, ischiocavernosus muscle, nerves innervating the ischiocavernosus muscle, or any combination thereof.

16. A method for electrifying nerves and/or muscles of a perineum of a subject, comprising:
    positioning a device configured to deliver an electric field to selected targets in the perineum to the perineum skin between a posterior aspect of a scrotum and an anus of said subject, said device comprising an attachment element configured to attach a surface of said device to a perineal surface of said subject and to keep said device attached to said perineum between said posterior aspect of the scrotum and said anus during sexual intercourse;
    generating said electric field by a pulse generator of said device, according to at least one electric field parameter comprising a pre-determined intensity level and at least one treatment program comprising a ramp time of at least 5 seconds, whereby said generated electric field increases to reach said pre-determined intensity level during said ramp time; and
    delivering said electric field to said nerves and/or muscles of the perineum by at least two electrifying electrodes of the device,
    wherein said electrifying electrodes are disposed entirely on a skin surface between said posterior aspect of the scrotum and said anus; and
    said at least one electric field parameter, including said intensity level, and said at least one treatment parameter, including said ramp time, are selected to inhibit rhythmic contractions of said bulbospongiosus muscle and delay an ejaculation in said subject during said delivery of said electric field when said device is attached to said perineum surface during said sexual intercourse.

17. The method of claim 16, further comprising measuring, by at least one sensor in said housing, at least one physiological parameter.

18. The method of claim 16, further comprising measuring, by at least one electrode or sensor of said device, impedance of the generated electric field and one or more, by said device, of:
    generating a human detectable indication when values of said measured impedance are higher than 3000 ohm; and
    stop generating said electric field if said measured impedance values are higher than 5000 ohm.

19. The method of claim 16, further comprising:
    measuring, by at least one electrode or sensor said device, values of at least one electrical parameter of the electric field; and
    calculating, by said control circuitry, impedance based on said measured values of said at least one electrical parameter of the electric field.

20. The method of claim 16, further comprising:
    measuring, by at least one sensor or electrode electrically connected to said control circuitry, values of at least one physiological parameter of said subject; and
    generating, by said pulse generator, said electric field if said measured values are higher than a predetermined value and/or if said measured values are in a desired range.

* * * * *